US012614626B2

(12) United States Patent
Troxler et al.

(10) Patent No.: US 12,614,626 B2
(45) Date of Patent: Apr. 28, 2026

(54) METHODS AND APPARATUS FOR PREDICTING AND PREVENTING AUTISTIC BEHAVIORS WITH LEARNING AND AI ALGORITHMS

(71) Applicants: Isabelle Mordecai Troxler, Raleigh, NC (US); Robert Ernest Troxler, Raleigh, NC (US)

(72) Inventors: Isabelle Mordecai Troxler, Raleigh, NC (US); Robert Ernest Troxler, Raleigh, NC (US)

(73) Assignee: Isabelle Mordecai Troxler, Raleigh, NC (US)

( * ) Notice: Subject to any disclaimer, the term of this patent is extended or adjusted under 35 U.S.C. 154(b) by 91 days.

(21) Appl. No.: 17/812,078

(22) Filed: Jul. 12, 2022

(65) Prior Publication Data

US 2023/0021336 A1 Jan. 26, 2023

Related U.S. Application Data

(60) Provisional application No. 63/220,985, filed on Jul. 12, 2021.

(51) Int. Cl.
*G16H 20/70* (2018.01)
*G06N 5/022* (2023.01)

(52) U.S. Cl.
CPC ............. *G16H 20/70* (2018.01); *G06N 5/022* (2013.01)

(58) Field of Classification Search
CPC ........... G16H 20/70; G06N 5/022; G06N 3/04
See application file for complete search history.

(56) References Cited

U.S. PATENT DOCUMENTS 4,093,821 A * 6/1978 Williamson ............ G10L 25/90
704/207
7,034,695 B2 4/2006 Troxler
(Continued)

FOREIGN PATENT DOCUMENTS

WO WO-2020257352 A1 * 12/2020 ......... A61B 5/02055

OTHER PUBLICATIONS

Taj-Eldin et al, "A Review of Wearable Solutions for Physiological and Emotional Monitoring for Use by People with Autism Spectrum Disorder and Their Caregivers," Sensors 2018, 18, 4271; doi:10.3390/s18124271. (Year: 2018).*

(Continued)

*Primary Examiner* — Jonathon A. Szumny
(74) *Attorney, Agent, or Firm* — NK Patent Law PLLC

(57) ABSTRACT

The subject matter described herein includes methods and systems for predicting and preventing negative behaviors with learning and AI algorithms. According to one method, physiological data of a user is measured. For example, using sensors located on the user. A stress level of the user is determined based on the measured physiological data. An intervention is then determined for adjusting the stress level of the user in response to the stress level being at least one of outside or nearing outside of a baseline range of the user. According to one system, at least one sensor measures physiological data of a user. An analysis device, such as a mobile device or remote server, determines a stress level of the user based on the measured physiological data and determines an intervention for adjusting the stress level of the user in response to the stress level being outside or nearing outside of a baseline range of the user.

30 Claims, 13 Drawing Sheets

(56) References Cited

U.S. PATENT DOCUMENTS

| | | | | |
|---|---|---|---|---|
| 7,848,905 | B2 | 12/2010 | Troxler et al. | |
| 8,326,635 | B2 * | 12/2012 | Usher | H04R 1/10 |
| | | | | 704/274 |
| 9,445,184 | B2 | 9/2016 | Ring | |
| 11,284,834 | B1 * | 3/2022 | Milbert | G16H 40/63 |
| 11,483,513 | B1 * | 10/2022 | Waggoner | H04N 5/60 |
| 2001/0016048 | A1 * | 8/2001 | Rapeli | H03G 3/32 |
| | | | | 381/104 |
| 2006/0293838 | A1 * | 12/2006 | Yamamoto | G09B 19/00 |
| | | | | 701/532 |
| 2009/0234586 | A1 * | 9/2009 | Tanaka | G01N 33/6812 |
| | | | | 702/179 |
| 2009/0264711 | A1 * | 10/2009 | Schuler | A61B 5/165 |
| | | | | 600/300 |
| 2013/0013208 | A1 * | 1/2013 | Ohnemus | G16H 50/30 |
| | | | | 702/19 |
| 2013/0060150 | A1 * | 3/2013 | Song | A61B 7/003 |
| | | | | 600/529 |
| 2013/0195302 | A1 * | 8/2013 | Meincke | H04R 25/356 |
| | | | | 381/321 |
| 2013/0225950 | A1 * | 8/2013 | Van Elswijk | G16H 10/20 |
| | | | | 600/309 |
| 2014/0111690 | A1 * | 4/2014 | Kim | H04N 21/42201 |
| | | | | 348/565 |
| 2015/0331941 | A1 * | 11/2015 | Defouw | H04N 21/26258 |
| | | | | 707/687 |
| 2017/0143246 | A1 * | 5/2017 | Flickinger | A61B 5/6898 |
| 2017/0339484 | A1 * | 11/2017 | Kim | A61B 5/165 |
| 2017/0360356 | A1 * | 12/2017 | Ashdown | G16H 20/40 |
| 2018/0032682 | A1 * | 2/2018 | Donalds | G16H 30/20 |
| 2018/0107943 | A1 * | 4/2018 | White | G06N 5/01 |
| 2019/0009077 | A1 * | 1/2019 | Lazarus | A61N 1/0551 |
| 2019/0045020 | A1 * | 2/2019 | Ein-Gil | A61B 5/165 |
| 2019/0232974 | A1 * | 8/2019 | Reiley | G06V 40/168 |
| 2019/0246982 | A1 * | 8/2019 | Mackellar | A61B 5/291 |
| 2019/0267121 | A1 * | 8/2019 | de Sousa Moura | G16H 50/20 |
| 2019/0307388 | A1 * | 10/2019 | Bobo | A61B 5/7282 |
| 2019/0336724 | A1 * | 11/2019 | Li | A61B 5/165 |
| 2020/0058404 | A1 * | 2/2020 | Nazem | G16H 20/60 |
| 2020/0075039 | A1 * | 3/2020 | Eleftheriou | G06V 40/20 |
| 2020/0107778 | A1 * | 4/2020 | Goldstein | A61B 5/486 |
| 2020/0143924 | A1 * | 5/2020 | Ilan | G16H 20/10 |
| 2020/0152330 | A1 * | 5/2020 | Anushiravani | G16H 70/60 |
| 2020/0234814 | A1 * | 7/2020 | Theory | G06F 3/013 |
| 2020/0302825 | A1 * | 9/2020 | Sachs | H04N 21/472 |
| 2021/0000405 | A1 * | 1/2021 | Smets | A61B 5/389 |
| 2021/0154430 | A1 * | 5/2021 | Lev | G06F 3/011 |
| 2021/0306771 | A1 * | 9/2021 | El Guindi | A61B 5/053 |
| 2021/0319905 | A1 * | 10/2021 | Monaghan | G16H 50/30 |
| 2021/0321923 | A1 * | 10/2021 | Dobrovolná | A61B 5/165 |
| 2021/0353903 | A1 * | 11/2021 | Park | A61B 5/486 |
| 2022/0095973 | A1 * | 3/2022 | Luciani | G16H 10/60 |
| 2022/0108624 | A1 * | 4/2022 | Kwatra | G06V 20/41 |
| 2022/0157434 | A1 * | 5/2022 | Srour | G16H 40/67 |
| 2022/0172836 | A1 * | 6/2022 | Neumann | G16H 50/20 |
| 2022/0272465 | A1 * | 8/2022 | Boldt | A61B 5/165 |
| 2022/0296847 | A1 * | 9/2022 | Freckleton | A61B 5/681 |
| 2022/0301666 | A1 * | 9/2022 | Shluzas | G06N 3/04 |
| 2022/0346640 | A1 * | 11/2022 | Hamrah | A61F 9/0017 |
| 2022/0375572 | A1 * | 11/2022 | Altman | G16H 50/20 |
| 2022/0415462 | A1 * | 12/2022 | Vodencarevic | A61B 5/0022 |
| 2023/0016667 | A1 * | 1/2023 | Srour | A61B 5/6815 |
| 2023/0181074 | A1 * | 6/2023 | Amthor | A61B 5/7275 |
| | | | | 600/411 |
| 2023/0395235 | A1 * | 12/2023 | Rajput | A61B 5/162 |
| 2024/0090808 | A1 * | 3/2024 | Bhowmik | A61B 5/6817 |

OTHER PUBLICATIONS

Petrescu et al., "Integrating Biosignals Measurement in Virtual Reality Environments for Anxiety Detection," Sensors 2020, 20, 7088 ; doi:10.3390/s20247088. (Year: 2020).*

Sheikh et al., "Wearable, Environmental, and Smartphone-Based Passive Sensing for Mental Health Monitoring," Front. Digit. Health 3:662811; doi: 10.3389/fdgth.2021.662811. (Year: 2021).*

"B-Calm Headphones". National Autism Resources. Accessed on Aug. 2, 2022. https://nationalautismresources.com/b-calm-headphones/.

"Improve focus and attention now with Revibe Connect" and "Learn more about our future tech: Digital therapy for ADHD". Revibe. Accessed on Aug. 2, 2022. https://www.revibetech.com/.

"A Fusion of Technology and Behavioral Science". Revibe. Accessed on Aug. 2, 2022. https://www.revibetech.com/our-science.

"Our Future Technology: The Next Big Thing in ADHD Therapy Is Coming". Revibe. Accessed on Aug. 2, 2022. https://www.revibetech.com/our-future-technology.

* cited by examiner

| Adaptive Controller | Bayesian Statistics | Genetic Control |
| Artificial Intelligence | Machine Learning | Expert Systems |
| Real Intelligence | Reinforcement Learning | |
| Neural Networks | Fuzzy Logic | |

Output

| Table | Selected |
|---|---|
| Manual | Selection |
| Autonomous | Selection |
| | Learning Algorithm |

| Sensor | Select | Output | Feed Back |
|---|---|---|---|
| A | Familiar Voice Phrase | Sound | Improving |
| B | Music Selection | Volume | Increasing |
| Z | Haptic Massage | Intensity | Decreasing |
| | | Video | |

METHODS AND APPARATUS FOR PREDICTING AND PREVENTING AUTISTIC BEHAVIORS WITH LEARNING AND AI ALGORITHMS

CROSS REFERENCE TO RELATED APPLICATIONS

This application claims priority to U.S. Provisional Patent Application No. 63/220,985 filed on Jul. 12, 2021, entitled "Methods and Apparatus for Predicting and Preventing Autistic Behaviors with Learning and AI Algorithms", which is incorporated by reference herein in its entirety.

FIELD OF THE INVENTION

The present invention relates to proactive intervention for users with sensory processing difficulties, and more specifically, to methods and apparatus for predicting and preventing negative sensory overload responses with learning and AI algorithms.

DESCRIPTION OF RELATED ART

According to JAMA Pediatrics, one in six children have sensory processing difficulties. In specific populations, the prevalence of difficulty processing sensory inputs is estimated to be as high as 80%-100%. This includes, for example, children with autism spectrum disorders, fetal alcohol syndrome, prematurity, down syndrome, ADD/ADHD, anxiety attacks, and others. The latest estimate from the National Center for Health Statistics reports that 7.5% of American children were medicated for "emotional or behavioral" difficulties in 2012. One in 54 American children is diagnosed with an Autism Spectrum Disorder (CDC, 2016) which often has profound impacts on learning and familial and social relationships.

A child with sensory processing difficulties can either be over-responsive or under-responsive to a particular sensory input. Children who are hypersensitive are over-responsive to sensory stimulation, whereas children who are hyposensitive are under-responsive to sensory stimulation. The same child can be hypersensitive to many stimuli, but hyposensitive to others, which requires careful monitoring, deep understanding, and complex care needs from family members, teachers, and other caretakers.

Hypersensitive children often experience what is called "sensory overload" where both typical and extreme stimuli, such as lights and smells, can impact, and cause hypersensitive children to act out of frustration. This may be especially true when verbal communication is limited, and an adult is not aware that the trigger is present or approaching.

Hyposensitive children, in contrast, may be under-responsive to body signals that affect coordination and balance or less responsive to pain signals from their body, resulting a high pain tolerance and potential injurious behavior. In a similar way to their hypersensitive peers, this low level of reaction to sensory inputs often results in a desire for sensory heightening. When this does not happen, combined with limited verbal communication, adults or guardians are often not aware of the trigger, or state of stress, and behavioral outbursts occur as a result.

Children with sensory processing difficulties can have frequent meltdowns, such as crying, screaming, kicking, collapsing, having self-injurious behavior, or aggression, that can potentially interfere with daily functioning and their ability to learn.

The sensory processing difficulties experienced by children may be inadequately addressed by even the most attentive adult or guardian because of communication barriers between children diagnosed with these conditions and those around them. Children with sensory processing disorders may also have associated speech difficulties. For example, 75% of children aged 0-14 with an autism diagnosis may have extremely limited verbal communication skills. This disconnect between affected children and unaffected adults and siblings or peers, often causes frustration in the children when they are not able to communicate their wants and needs, sometimes resulting in violent and disruptive behavior.

Children diagnosed with autism, as an example of a condition associated with sensory processing difficulties, are often very sensitive to sound and their environment. Once children diagnosed with autism become overstimulated, they may require a calm, personal, and distraction-free space with proper sound to calm down, re-focus, and stop a vicious cycle of frustration and outbursts.

To break this cycle, or to prevent frustration and outbursts from occurring initially, it is critical to properly analyze and react to early signs of sensory over- or under-stimulation. These signs are referred to as "stress precursors" and include some of the earliest measurable physiological indications of frustration. If left unchecked, these stress precursors may result in sensory overload, frustration, and behavioral outbursts.

Accordingly, a need exists for improved methods and apparatuses for predicting and preventing unnecessary suffering of individuals/subjects and consequently negative behaviors and distractions or harm to those also present.

BRIEF SUMMARY

The subject matter described herein includes methods and systems for predicting and preventing negative sensory overload with learning and AI algorithms. According to one method, physiological data of a user is measured. For example, using sensors located on the user. A stress level of the user is determined based on the measured physiological data. An intervention is then determined for adjusting the stress level of the user in response to the stress level being outside of a baseline range of the user.

According to one system, at least one sensor measures physiological data of a user. An analysis device, such as a mobile device or remote server, determines a stress level of the user based on the measured physiological data and determines an intervention for adjusting the stress level of the user in response to the stress level being outside of a baseline range of the user.

DETAILED DESCRIPTION

Figure 1:
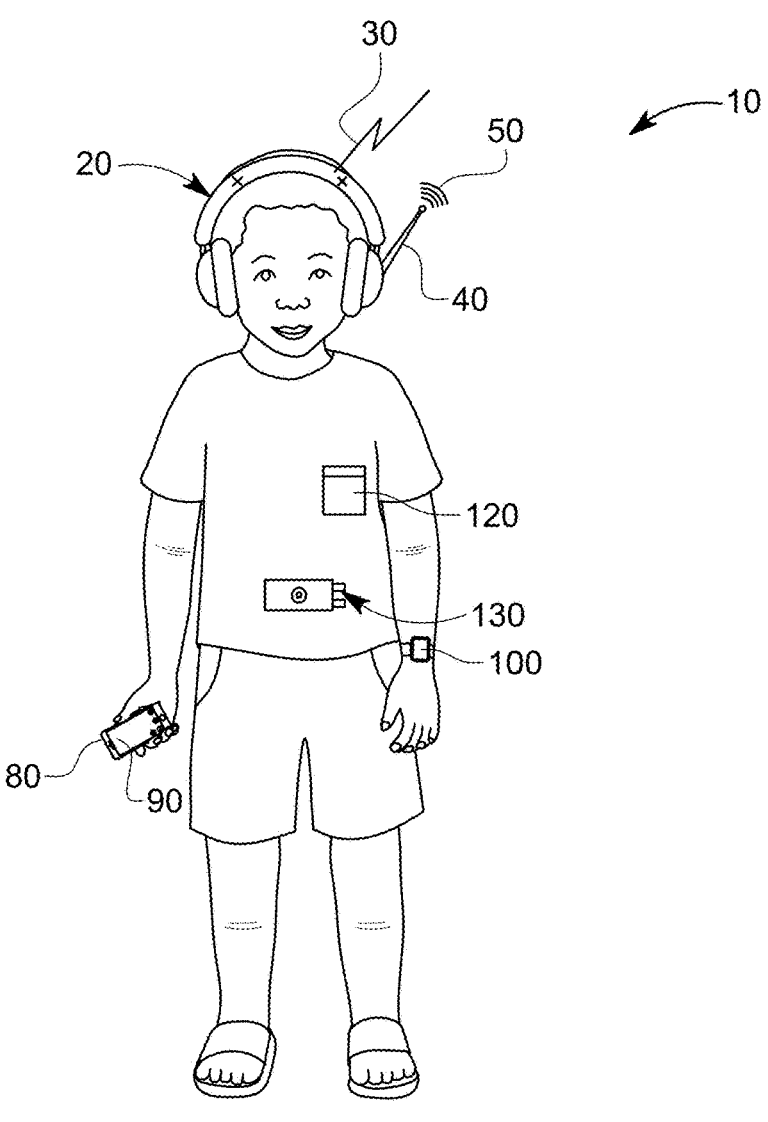
FIG. 1 is a diagram illustrating a subject, such as a child, wearing headphones according to an embodiment of the subject matter described herein.

The subject matter described herein includes methods and systems for predicting and preventing negative behaviors incorporating learning and AI algorithms. According to one method, physiological data of a user is measured. For example, using sensors located on the user. A stress level of the user is determined based on the measured physiological data. An intervention is then determined for adjusting the stress level of the user in response to the stress level being outside of a baseline range of the user.

According to one system, at least one sensor measures physiological data of a user. An analysis device, such as a mobile device or remote server, determines a stress level of the user based on the measured physiological data and determines an intervention for adjusting the stress level of the user in response to the stress level being outside of a baseline range of the user.

In contrast to conventional configurations for users with sensory processing difficulties which simply react or rather are reactionary to the external manifestations of a user's stress level, such as outbursts or tantrums, the present disclosure proactively monitors and analyzes the user's physiological and other data to determine the user's stress level before an outburst occurs and proactively intervenes to prevent the outburst.

For example, a system according to the subject matter described herein may broadly be divided into three functional categories. The first category of devices includes sensors and other input devices for obtaining, measuring, receiving, monitoring, recording, or otherwise determining various types of data which are used as input to the system. The second category includes computer processors, controllers, memory, computer-executable instructions, and other circuitry for processing the data provided by the input devices. The third category includes various devices for mediating one or more sensory inputs of a user based on the analysis performed by the data processing components. These devices may be for example mechanical and/or electrical in principle and perform the task of responding or are reactionary to the output of the system. While each of these categories may include multiple, separate, non-overlapping devices, it is appreciated that the functionality associated with multiple categories may also be integrated into the same device.

Input devices and sensors may be further divided into two groups: external conditions and internal physiological conditions.

Sensors that measure the external conditions of the user's surroundings may include, for example, microphones for measuring sound, cameras for measuring images, light sensors for measuring a color temperature or brightness of light, motion sensors for measuring nearby movement of objects, temperature sensors for measuring the temperature of the user's surroundings, and location sensors for measuring the user's location. It is appreciated that any type of sensor capable of measuring or detecting environmental conditions may be used without departing from the scope of the subject matter herein.

It is also appreciated that the user may have corollary sensory organs for detecting the same external conditions. For example, "sensory input" describes the response in a sensory organ (eyes, ears, nose, tongue, and skin) when it receives stimuli. Sensory input is most often defined as the stimulation of a sense organ that causes a nerve impulse to travel to its appropriate destination in the brain or spinal cord. As used herein, "sensory input", "physiological measurements", "physiological conditions", and "biometrics" refer to the stimulation of a sensor other than a sense organ of the user and consists of various sensors that measure the activity in bodily systems in response to things that are experienced through our senses or imagined.

The selection of sensors is important because the information they collect is correlated with the information (stimuli) experienced by the user's senses (e.g., taste, touch, sound, sight, smell). This allows the system to be aware of the same stimuli that the user experiences. Without this information, it may be difficult to determine, for example, whether a user's heartrate is high because a sound is too loud (or too soft) or because a light is too bright (or too dark).

Other sensors measure physiological aspects of the user such as heartrate, body temperature, and skin excitation. While these physiological conditions may be an output of the user, they are an input to the system described herein. For example, a loud noise may be detectable by both a microphone worn by the user and the user's ears. The user's reaction to the sound may include an elevated heartrate, which is also measurable by the system using a heartrate sensor.

Exemplary measurement sensors include, but are not limited to, an EKG, ECG, infrared temperature sensor, accelerometer, brain wave sensor, vibration sensor attached or monitoring the user's body, sound and movement sensors, breathing sensor, eye movement sensor, muscle tension sensor, or a sensor for measuring any biological or neurological response relating to a controllable or uncontrollable behavior. Exemplary measurement sensors also include a cardiovascular monitor, a core temperature measurement sensor, an ear measurement, a pulse sensor, and other invasive or non-invasive sensors.

In one embodiment, multiple sensors may be located on the same device such as a smartwatch worn around the user's wrist. Such a device may include a first sensor for measuring the user's heartrate (internal physiological conditions) and a second sensor for measuring any sound or noise (external environmental conditions). It is appreciated that these two sensors may be integrated within the same smartwatch device and/or that more than these two sensors may be part of the same smartwatch device. Other sensors may be embedded in a collar or band worn by the subject.

In other embodiments, multiple separate sensors are distributed in different locations and are not all physically integrated within the same device. For example, a microphone may be integrated with a pair of noise-canceling headphones or earbuds, a smart clothing sensor may be integrated with the user's shirt, and a heartrate monitor may be integrated with a smartwatch.

Each of these devices may use different and/or overlapping communications technologies for transmitting data to other devices. The system described herein can be configured to receive data from a variety of sensors using a variety of communications technologies including Bluetooth, WiFi, and the like. For example, data provided by the sensors may be sent to a nearby mobile device such as a phone, tablet, or laptop.

The data received from the sensors is then used to determine which, if any, actions are necessary to calm the user. Typically, this includes mediating the sensory input(s) experienced by the user/subject by enhancing, suppressing, or changing those inputs. For example, auditory sensory input may be mediated by blocking or muffling environmental sounds using a pair of earbuds or headphones. Auditory sensory input may be also filtered, removed, or mediated by selectively enhancing or suppressing different frequency ranges using noise-canceling earbuds or headphones. Auditory sensory input may be also mediated by increasing the volume of environmental sounds using headphones. Lastly, auditory sensory input may be mediated by substituting the sound of the user's environment with pre-recorded sounds that are provided to the user. For example, music may be played in the user's headphones instead of the sound that would otherwise be heard by the user. Interventions can be implemented or performed using one or more invasive or non-invasive outputs, control devices, and/or output control devices.

It is appreciated that other sensory inputs can also be mediated in this manner. For example, smart glasses, sunglasses or VR headsets may be used to mediate visual input. Different users (or different outputs) may prefer or require not only different types of mediation of their sensory input (increasing vs. decreasing sensitivity) but may also prefer or require mediating different types of sensory input (audio vs. visual input).

The determination as to whether to increase, decrease, or substitute the sensory input of a user may be to achieve a change in the user's state, as measured by the input sensors. such changes could be calming a child back to a baseline level further indicated by their heartrate or other factors. This determination may be performed automatically and autonomously where the system continuously monitors the stress level of the user, as indicated by a comparison of the user's sensory input data with a baseline model for the user.

If the user's stress level begins to rise, as indicated by trend lines of one or more stress precursors, the system may automatically determine a probable action to lower the user's stress level. This process of monitoring sensory input data, evaluating whether action should be taken, and re-evaluating the sensory input data to determine whether the action was successful or whether more, different, or a combination of actions should be taken, is a feedback loop that provides continuous monitoring and prevents the user from becoming further stressed. As mentioned above, the capacity to intervene early is key to protecting children, their caretakers, and improving the lives of anyone in their environment from stress, chaos, and turmoil, and setting children (or adults) on a path of peace, understanding, and success. Arguably the most debilitating, and outburst causing, components of sensory processing disorders, such as autism, lie in the lack of typical verbal communication skills. Through the use of PPR devices, subjects will be projected to levels of understanding unlike ever before. The result is for subjects themselves to be able to use the devices, learn from them, and over time gain greater understanding of their own triggers and needs, and reduce negative behaviors before they begin. Additionally, caretakers will have the same opportunity with a user-friendly interface to understand the needs of their loved one(s) deeply, even without verbal exchange, and prevent time-wasting, distracting, and hurtful behavior outbursts, and provide a much higher quality of care, education, and support in activities of daily living. Contentment, ability to focus and learn, relationships with others, self-awareness and regulation, and overall quality of life shows promise of improvement. Example precursors may include, but are not limited to: gradual-but-steady rise or fall in heart rate, sudden rise or fall in heart rate, irregularity between heartbeats, rise or fall in blood pressure, irregular change in body temperature, irregularity in movement/steps per minute/hour/day, onset of repetitive or frantic noises coming from the child, less or more than baseline calories burned, less or more than baseline calories consumed or change in types of food eaten (ex: many more carbs vs. protein and fats than is consistent with baseline), irregularity in sleep cycles and heart rate during sleep, differences or irregularity in self-reported mood tracking, and irregularity in EEG brain wave monitoring.

It is appreciated that action may be taken to lower the user's stress level, including mediating the user's sensory input(s), even before the user moves out of their baseline range.

As will be discussed in greater detail below, the determination of which, if any, actions should be taken in response to the sensory input data may be different depending on the mode in which the system is operating. In a learning or training mode, the received input data may be recorded for analysis without taking any action. In an operational mode, however, the received input data may not be recorded, and the analysis performed during learning mode may be used to determine which actions are taken in response. It is also appreciated that the system may operate in a hybrid mode that includes aspects of both the learning mode and the operational mode. For example, while in the operational mode, a subset of the input data may be recorded, and different actions may be tested, to improve the performance of the system.

One goal of the learning mode is to build a user profile or baseline model for the user. The user profile includes values, or ranges of values, for a variety of input data types. These values may be collected from a variety of sensors located on or near the user or may be provided from other sources (e.g., manually entered, from a database, etc). For example, input data may include one or more of the following: heart rate or pulse, heart rhythm, acceleration, location, sweat, eye movement, body temperature or fever, skin temperature, muscle tension, blood pressure, physical activity or movement, neurological activity, muscle spasms, shaking, jittering, blood oxygen levels, deterministic optical spectroscopy analysis, blood flow, environmental acoustical measurement, acoustic, audible, or voice noise from the user, sleep cycles, skin impedance all as a matter of example.

Input data in the user profile that is received from sources other than from sensors may include one or more of the following: medical diagnosis, self-reported mood, self-reported calories consumed, self-reported calories burned, self-reported nutrition information, information from blood tests, information from allergy tests, medication, self-reported activity level, psychological testing for any mental disorders, and implanted devices that deliver drugs, monitor conditions, or treat diagnoses by stimulating the brain with light or electricity.

Similarly, example input sensors may include one or more of the following: ear plugs, hearing aids, eyeglasses with visual, mechanical, or audio stimulation, 2D and 3D imagery such as in an Ocular device, acoustic bone conduction devices, gaming device, wearable device, haptic devices, smartwatch, finger sensor, cavity or surrounding sensors, scalp electric field sensors, EKG and EEG sensors, smart clothing sensors, smart watch, torso or body position and acceleration sensors, GPS, beacon, indoor tracking, accelerometers, dead reckoning, accelerometers. Although some of these sensors are related to location or identification, it is appreciated that any physiological precursor, movement or mood sensor, or biofeedback sensor can be incorporated as inputs to the system.

In addition to the process of creating a user profile without any prior knowledge of the user, the system may use a predetermined profile that is not specific to the user and then refine the profile with information that is specific to the user. This may accelerate the process of building the user profile by reducing the amount of time operating in the AI learning mode.

For example, data may be collected and aggregated from multiple users that share similar sensory processing difficulties such as children between the ages of 7-10 with hypersensitivity to sound. An analysis of this aggregated data may determine that the average resting heart rate for these users or subjects ranges from 70 to 75 bpm. As a result, a new user having similar characteristics may have their user profile pre-populated with this a priori knowledge and this may be modified during the learning mode to be specific to the particular user. The use is not restricted to children. Adults, men, women, and animals are also valid classifications.

The user profile may be created and maintained by a computer application on, for example, the user's mobile device. The application may receive feedback based on gathered data. For example, if the user were to wear headphones and a smartwatch for two weeks, the client or caretaker could download the app and enter basic information such as name, date of birth, age weight and other pertinent data. Other fields in the user profile for creating a baseline may automatically be gathered. This user profile information presented in the app may look something like the following:

```
Predict, Protect, and Redirect
Welcome
Name: Jane Doe
DOB: 01/01/2008
Statistics
Weight
Height
Resting Heart Rate: 72
Max heart rate recorded: 201
Average heart rate when active: 115
Blood Pressure: 100/57
Body Temperature: 98.2
Average steps Per Minute: 40
Average steps per hour: 2,075
Average steps per day: 12,589
Average peak activity times: 7-10am, 3-5pm
Average calories burned: 2,460
Heartbeat interval regularity: *click to see graph
Sleep cycle chart: *click to see graph
EEG brain wave averages: *click to see graph
View irregular input here
```

The user will be able to choose from a daily, weekly, or monthly selection to see all information from the selected time range. The user can click on a specific date, such as Jul. 1, 2021, to see the averages on that specific day. The user can also click on a weekly view, with graphs charting each area. Once data has been collected for at least a month, monthly averages can be viewed, and so on. Projections and trends are also reportable.

If a caretaker has more than one child using the system, the caretaker may manage multiple children using the App. The caretaker can click upon the child they wish to view upon logging into the Application to manage settings and monitor data for the selected child.

If the user clicks "view irregular input" for the child, an easy-to-read visual presentation may be provided. The visual presentation may include time stamps and durations, which may appear across day, week, or month for that child, notifying the caretaker when, for how long, and in what area there was irregular input. The App may also include a notetaking function for tracked written notes of when notable mood swings or outbursts occurred. This will quickly provide the App user/administrator with knowledge that will allow for early intervention.

During the learning mode, input data may be recorded for analysis. Recording the input data may include receiving and storing the data over a period of time. Storage of the input data may be done locally or remotely. Local storage may include the same device as the sensor that collected the data, such as a smartwatch configured to store heartrate or specific body temperature information collected by the smartwatch. Specific temperature may include a patient back or side while bedridden. In other cases, information collected by a sensor may be transmitted to a nearby device for storage, such as a smartphone, tablet, or laptop. In yet other cases, information collected by sensors may be transmitted to a remote server or the cloud for storage.

It is also appreciated that a single device can store multiple types of data, and that the data can be stored in multiple locations. For example, data may be stored locally on a smartwatch that collected the information, and on a mobile phone that received the information from the smartwatch via Bluetooth, and on a remote server that received the information from the mobile phone via WiFi, or in the wearable headphone system.

While children are different, there are certain characteristics or categories that groups of children may exhibit. For example, some children are sensitive to audio, some are more sensitive to visual stimuli, and some have other sensory issues, with all the combinations between. The headphones disclosed herein have a learning mode where the parent, guardian, caretaker, child, and smart device like headphones determine a behavioral baseline and limits. This learning phase may include using an application specific program on a tablet, laptop, or smart phone where a parent grades the child's behavior and the system records inputs of the sensory system of the child or subject. For example, on a "good day" when minimal negative behaviors are observed, the temperature of the subject is within set limits of 97° F. to 99° F., heart rate, blood pressure, skin properties are also being recorded.

These recorded inputs may also be classified into tiers. Example classification tiers could include bad, average, good, and great behavior classifications. Other classifications could include the type of behavior such as tantrums, head banging or total lock down and responsiveness. The classification could be with respect to the end behavior of the subject. For example, if the body temperature starts to rise and cardiovascular system starts to show some stress signs, the parent or guardian may use the App to grade the behavior in real time through the point in time when the subject's behavior starts to become undesirable. Since the headphone system (or smart watch or heads up display) records data in real time, with time this learning process can become predictable.

Once a database of information for a user has been created and populated, curve fitting and programming can be used to predict which state the subject is transitioning to and if the issues are increasing or decreasing. This could come from sensory data such as temperature, heart rate, blood pressure, voice, and eye or body movement. The result is a mapping of inputs of sensory data to predict and control the subject's behavior. Another aspect of the learning process is what works to calm the subject. Examples that the parent may present to the child could be prerecorded music, voices, massaging, or images presented on a heads-up display that tend to work well with this particular subject. Their favorite golden retriever video clips or other recordings, for example.

There may also be general classifications that can be tailored to a particular target. The headphones could be programed from the factory with these general behavior curves and responses needed to optimize or rather minimize unwanted or harmful behavior. These general curves could be based on case histories and used to train and test the behavior models. The models can be refined to be specific to the individual. Optimization and personalization may be performed using techniques including Artificial Neural Networks, deterministic procedures, instance-based learning models, pattern recognition tools, pattern matching where the subject is compared to previous or stored patterns, ensemble learning algorithms, and Bayesian mapping to name a few.

The inputs from the sensory measurements could form an input vector, these input vectors are used to classify according to stored patterns of behavior or from new categories if no categorical match is determined. No stored patterns are modified unless it matches the input vector within some tolerance.

The input vectors could represent the subject's temperature, heart rate, rhythm, acoustic or voice noise, skin impedance, sweat, biometric inputs from a smart watch or wearable. The learning phase could be a trial-and-error tuning process. The vectors could be weighted with coefficients for determining the proper response; the response being the music, massaging, vibrating or even suggesting a weighted blanket, swinging, ball bouncing, noise cancellation, a quiet, dark space, for example, to be suggested to the caretaker. In some responses the caretaker is instantly notified, and manual intervention may be the early choice. For instance, moving the subject to a different environment. However, means for automatically distributing a weighted blanket (for example) to or onto the subject are also contemplated.

Another attribute the headphones can do is determine when the child may be getting the flu or some other illness. For example, a sore throat could be detected by the subject changing the timber of their voice (audio) as its painful to scream or talk. Fever detected by the inner ear temperature or skin temperature. Hunger by a growling stomach, chills by jittery motion. Using connections to a cloud database, such as links to the CDC, the illness could be diagnosed and determined by knowledge of current outbreaks and symptoms exhibited by the subject. This analysis could be by video or some other communication from a physician on call or automatically through deep learning, machine learning or generally artificial intelligence. The internet of things approach could further be connected to each sensor or intervention device.

Machine learning (ML) is the use of computer algorithms that can improve system health or analysis automatically through experience and using real data. Machine learning algorithms build a model based on sample data, known as training data, to make predictions or decisions without being explicitly programmed to do so. Machine learning algorithms are used where it is unfeasible to develop conventional algorithms to perform the needed tasks.

In certain embodiments, instead of or in addition to performing the functions described herein manually, the system may perform some or all the functions using machine learning or artificial intelligence. Thus, in certain embodiments, machine learning-enabled software relies on unsupervised and/or supervised learning processes to perform the functions described herein in place of a human user.

Machine learning may include identifying one or more data sources and extracting data from the identified data sources. Instead of or in addition to transforming the data into a rigid, structured format, in which certain metadata or other information associated with the data and/or the data sources may be lost, incorrect transformations may be made.

Similarly, machine learning-based software may load the data in an unstructured format and automatically determine relationships between the data. Machine learning-based software may identify relationships between data in an unstructured format, assemble the data into a structured format, evaluate the correctness of the identified relationships and assembled data, and/or provide machine learning functions to a user based on the extracted and loaded data, and/or evaluate the predictive performance of the machine learning functions (e.g., "learn" from the data).

In certain embodiments, machine learning-based software assembles data into an organized format using one or more unsupervised learning techniques. Unsupervised learning techniques can identify relationship between data elements in an unstructured format.

In certain embodiments, machine learning-based software can use the organized data derived from the unsupervised learning techniques in supervised learning methods to respond to analysis requests and to provide machine learning results, such as a classification, a confidence metric, an inferred function, a regression function, an answer, a prediction, a recognized pattern, a rule, a recommendation, or other results. Supervised machine learning, as used herein, comprises one or more modules, computer executable program code, logic hardware, and/or other entities configured to learn from or train on input data, and to apply the learning or training to provide results or analysis for subsequent data.

Machine learning-based software may include a model generator, a training data module, a model processor, a model memory, and a communication device. Machine learning-based software may be configured to create prediction models based on the training data. In some embodiments, machine learning-based software may generate decision trees. For example, machine learning-based software may generate nodes, splits, and branches in a decision tree. Machine learning-based software may also calculate coefficients and hyper parameters of a decision tree based on the training data set. In other embodiments, machine learning-based software may use Bayesian algorithms or clustering algorithms to generate predicting models. In yet other embodiments, machine learning-based software may use association rule mining, artificial neural networks, and/or deep learning algorithms to develop models. In some embodiments, to improve the efficiency of the model generation, machine learning-based software may utilize hardware optimized for machine learning functions, such as an FPGA.

The system described herein, such as PPR headphones and accompanying products, can be utilized in many ways, from intelligent noise-canceling headphones up to a data generating machine with self-implementing interventions, weighted blankets, indoor sunglasses, bounce balls, fidget toys, and more.

A smart watch device can be put on the child to track their heart rate, blood pressure, temperature, and activity. Once a profile is created for the user and a base-line calculation is determined, an alert may be generated at a device by the Predict, Protect and Redirect App when measured data are expected to begin trending off significantly from their baseline. This gives users the ability to intervene before any type of outburst occurs.

The system also assesses the environment around the user to determine what could be causing changes in the user's stress levels. This information may be used to determine what intervention may be needed, which can be implemented through headphones (and/or the other wearable products such as sunglasses, weighted blanket, weighted vest, bounce ball, hand gadget, tactile device, sensory pea pod, putty, swing/hammock, or simply isolation or a quiet space) worn by the user. The user's environment could be restricted to a hospital bed where the environment consists of a room for lighting control, a television, monitor, and music.

The system may include many pre-set sounds that can be played through the headphones (possibly managed through a wireless remote that is controlled by the adult). In one embodiment, four pre-set sounds that are believed to be the most effective in calming are: ocean waves, summer night, waterfall, and raindrops. The system headphones may provide additional levels of comfort and re-direction for a child by utilizing the option to play personal recordings into the headphones. These recordings would most likely commonly include: the voice of a parent or teacher who has been known to be the most effective in calming or redirecting the child, a recording of a favorite TV show line or theme song, or a recording of a favorite song or sound. Speakers and other in-room devices could also be controlled through the feedback system monitoring a patient's stress level. This system could consist of wearable sensors, sensors located on room objects or mounted in the room, and even sensors embedded in reactionary objects such as a controllable bed.

In one specific example, in the event that a child is acting out physically, an adult might repeat a phrase such as "calm body" that can be recorded and played. Alternatively, in the instance that a child is overwhelmed but highly musical and responsive to music, a favorite song of the child can be recorded and played. Alternatively, in the instance that a child responds well to the voice of a particular person, the voice of that person speaking calming words or singing the child's favorite song can be played. Alternatively, in the instance that a child needs a break from mentally or physically draining tasks, the voice of the child's favorite TV character saying something calming or funny can be recorded and then played. Virtual reality glasses, lenses, or a smart mask can also be part of the responding feedback including videos, or even vibrations and haptic responses.

Over time, the caretaker can learn which interventions work best for the child and in what situation(s). This allows the caretaker to quickly and efficiently intervene when an alert goes off. The self-informing watch can also be programmed to communicate to the headphones to automatically play a certain song or sound.

Feedback and control are used to track and monitor the physiological reactions of the individual being monitored including signals such as heart rate, blood pressure, temperature, and activity. The controls will be music and/or voice through the headphones, and other physical haptic resources that we produce (sunglasses, weighted blanket, weighted vest, bounce ball, hand gadget, sensory pea pod, putty, swing/hammock, or simply isolation or a quiet space). The physiological signals gathered after intervention may also be fed back to the system controller, which will adjust and remeasure signals. The goal of the system is stress reduction and measuring the effectiveness of each intervention is important input for the system. Artificial intelligence and/or neutral networks may also be used to gather feedback and control.

The subject of the PPR system described herein may wish to operate the device manually or partially manually wherein the user understands the application, the headphones, and the intervention tools, and is able to predict their own stress precursors and intervene on those they are caring for, or on themselves, early. Eventually, the user can minimize stress episodes all together through deeper self-awareness. For users that are unable to operate the device themselves, another caretaker can use the system to learn the user's typical physiological precursors and intervene on the user's behalf to minimize stress episodes. Haptic responses including vibrations, electrical stimuli, can be measured and optimized for the best response or excitation. Again, this can be manual, semi-manual as in a hybrid approach, locally or remotely.

Games may also be pre-programmed into the application, and a profile can be created for each user to align their favorite games and best interventions. Within these games, points, rewards or a currency can be earned as an incentive for positive intervention and calm down procedures. For example, if the subject is an animal, good behavior may result in a cookie or biscuit automatically delivered by a connected device. This connection could be wireless such as a bluetooth or Wifi link, including control by Alexa™

The headphones may be designed to look similar to popular headphones made simply for music streaming such as Bose or Beatz By Dre so that children of the pre-teen, teen stages, and even adults can wear them with ease and never worry about being viewed any differently than anyone else with typical headphones on.

In one embodiment, automatic response interventions may be performed until irregular input returns to normal. This automatic response intervention may be manually turned on or off. In other embodiments, the response interventions may be initiated solely manually. Interventions can be programmed for individual clients.

In an example intervention, Teacher Mrs. Jones opens the PPR Application. Because she is Max's teacher, she knows that Max is hypersensitive to loud noises, and that repetitive, but quiet, classical music is a helpful intervention when he is in a loud setting. She programs into his account for Bach's 5th symphony to play at a volume 5 when she clicks a button on the Application, which she will do when the class gets noisy, they are in an assembly, at recess, etc. Similarly, these actions could take place automatically, and in many cases would not require AI, as a measurement of conditions could electronically begin some process.

In another example intervention, Teacher Mrs. Jones opens the PPR Application. She knows, because of the data collected on Sarah by the headphones with previous monitoring, that although Sarah does not show any physical or verbal signs of distress that the application can identify stress before frustration becomes out of control. Input data may indicate that the heart rate skyrockets, her movements become repetitive, and her blood pressure rises. The administrator programs into her account for an audio recording of Sarah's favorite TV show to play when the irregular input starts, and gradually reduces the intervention as her heart rate, movements, and blood pressure return to normal. Seamlessly and autonomously through the AI engine.

In yet another example of intervention, Joaquin's mother Maria knows that her son struggles in the evenings, between dinner and bedtime, and that he often becomes restless and agitated when he knows bedtime is nearing. Because she volunteers in the classroom, she is aware that he is very attached to his teacher, Mrs. Jones, and that he responds well to her voice when she repeats "calm body". With a predetermined response, in this case a recording of Mrs. Jones repeating "calm body", she loops the track. The recording in this case was preprogrammed where the mother and Mrs. Jones worked together to store the audio clip into Joaquin's profile on the PPR Application. In this case, they both have access to the same database. Hence, if desired the APP can select this response and play it every evening at 7:30 pm until Maria decides to turn it off or it shuts down automatically The subject matter disclosed herein is discussed below with reference to the Figures which illustrate various aspect, features, exemplary implementations, or other embodiments. It is appreciated that these examples and illustrations are not intended to be limiting. The word "exemplary" is used herein to mean "serving as an example, instance, or illustration." Any embodiment described herein as "exemplary" is not necessarily to be construed as preferred or advantageous over other embodiments.

FIG. 1 is a diagram illustrating a subject wearing sensory input-mediating headphones according to an embodiment of the subject matter described herein. Referring to FIG. 1, a user (also referred to herein as a "subject") such as a child 10 is shown wearing one or more sensory input-mediating devices 20. Here, the one or more sensory input-mediating devices 20 include headphones and are referenced as headphones 20 for simplicity. In one embodiment, a pair of active predict, protect, and redirect (PPR) sensory headphones includes two earphones connected by a headband. Each earphone includes an earphone body having a cup-shaped shell and a cushion. The headband exerts a force in an inward direction so that the cushion is urged against the head of a user and surrounding the ear to enclose an acoustic cavity which may include the outer ear and ear canal. The headphones 20 can monitor, for example, physiological information including: heart rate, heartbeat intervals, blood pressure, body temperature, movement, noise, calories used, sleep cycles, EEG brain wave monitoring. For example, temperature may be measured in the headphones using an infrared sensor pointed into the ear. Other input-mediating or reactionary devices may include a collar or band worn around the user or placed in or close to a body cavity. The headphones have both the sensors for measuring the state of the user and can perform a duty determined by the output of the system (or react) to aid in mediating the state of the user. The input sensors can also be separate from the mediating device. For instance, a massaging band or sock may have sensors embedded or may have sensors separately located.

Other sensory input-mediating devices 20, including smart sunglass, hearing aids, active blankets, haptic systems, massaging systems, bone coupled audio or sonics, 3D ocular gaming devices, audiovisual devices, or vibratory stimulants, may not all be illustrated but may also be worn by the subject 10. In one embodiment, one or more sensory input-mediating devices 20 includes an active PPR sensory watch 100 (Apple™ Fitbit™ fitness wearable or Android for example) that includes a malleable silicone strap with adjustable sizing. The watch includes a digital screen atop a main plate that displays the time, heart rate, steps taken, and calories burned in its automatic display setting. The watch tracks heart rate, blood pressure, glucose etc. through sensors on the bottom half of the main plate of the watch. The watch, therefore, can also monitor, for example, physiological information including: heart rate, heartbeat intervals, blood pressure, blood flow, body temperature, movement, noise, calories out, and sleep cycles. Body sensors 30, 120, 130 can provide biofeedback manifested as electric field, IR, UV, or electromagnetic signals including EKG and EEG waves.

The headphones 20, as well as other sensors or devices, can be placed anywhere on the body or clothing of the subject 10. For example, FIG. 1 shows additional sensors such as scalp electric field sensors or EKG sensors 30, smart clothing sensors 120, smart watch 100, and torso or body position and acceleration sensors 130. These sensors can provide the feedback to the system by measuring biological emissions such as stress, strain, temperature, track heart rate, rhythm, acceleration, location, movement, sweat, eye movement, temperature, blood pressure, and general activity including neurological activity, muscle spasms while providing this data to the system as input. The sensors and reactionary devices can also be placed on the skin 135 such as the torso, arm, leg, thigh, on or inside an accessible part of the body.

The PPR headphones, watch, and downloaded application may all be configured to work together to automatically gather information that can be provided to the user or their caretaker. This information can set the user on a path of greater self-awareness, self-care, health, and mood stabilization.

In addition to sensors, various non-sensor devices may be placed anywhere on or in the body or clothing of the subject 10. These devices may be configured to perform an action in response to an instruction provided by the system rather than to collect physiological data. Such non-sensor or mediating-reactionary-response devices may include, for example, actuators, vibrator, acoustic aids, visual aids, and mechanical aids. On the other hand, these performance or action oriented "response or responder" devices could have integrated sensors and be IOT connected to the system. They could also be linked to a massaging or robotic glove 140, wearable clothing such as an undergarment against the body, or overgarment, socks 140, smart compression socks or a controllable body suit as indicated in 150. A collar, wearable, band, or neck piece could also be integrated with responding stimuli, and/or input sensors 160.

Also shown in FIG. 1 is a cell phone 80 which can be carried by the subject 10 or a guardian. The cell phone 80 may execute an App 90 for AI programs, monitoring and communicating with the sensors and systems mentioned above, storing information provided by the sensors and systems, and performing computation and analysis on the stored information. In one embodiment, the application software 90 for the headset 20 can act as an intermediary communications link between the headset 20 and remote storage and/or computation entities, such as the cloud. In another embodiment, the application software 90 can act as a database for storing data where only the computation is performed remotely (e.g., in the cloud). In yet another embodiment, the application software 90 can act as an endpoint for communicating with the headset 20 and performing computation of data from the headset 20 on the cell phone 80 (without using the cloud) and controlling the "responder" devices. This communication could be any RF, WiFi, IEEE 802.11.xxx method. It could also be connected by wire on occasion or most or all of the time.

In one embodiment, the cell phone 80 is connected directly to the headphones 20 and is configured to notify a guardian when a condition is met. For example, the application software 90 on the cell phone 80 may generate and send or receive a notification, such as text message, email, or push message, to a designated URL or other identifier associated with the guardian when the measured sensor data for the child 10 is outside of the baseline range in their user profile or trending in a direction. This notification allows the guardian to intervene quickly to calm the child 10 and help them return to their baseline stress level by, for example, talking to the child via video chat or voice call. Messages could also be generated and communicated directly by the headphones or mediating device.

Figure 2:
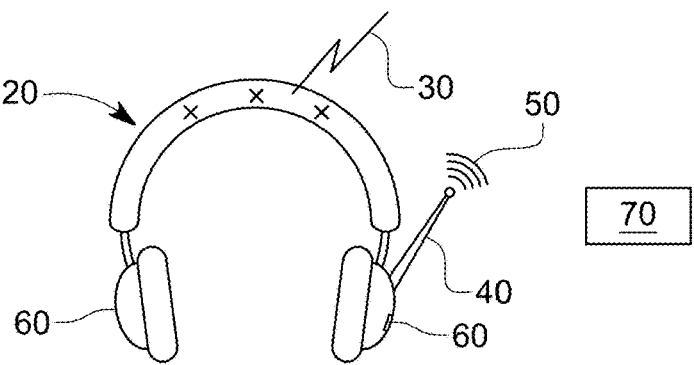
FIG. 2 is a diagram illustrating a headset consisting of scalp sensors for measuring voltages and small electric fields associated with the subject similar to an EKG according to an embodiment of the subject matter described herein.

FIG. 2 is a diagram illustrating a headset consisting of scalp sensors for measuring voltages and electric fields associated with the subject similar to an EKG-EEG according to an embodiment of the subject matter described herein. Referring to FIG. 2, the headset 20 consists of scalp sensors for measuring voltages and small electromagnetic fields associated with the subject, including an EEG. This data can be transmitted locally to cell phone 80 or to the cloud using antenna 40. Example communications technologies suitable for communicating data between the headset 20, the cell phone 80, and the cloud include, but are not limited to, IEEE 82.11.xxx technologies such as Bluetooth, Wi-Fi, or cellular connections. In one embodiment, a sim card 60 may be included in headset 20 for communicating via a cellular network and internet data transfers. One communication network may be preferable over other communication networks due to, for example, signal noise, coverage, or cost. Communications networks or communications technologies may be associated with a preference indicating whether, where, and when they should be used. One communication network may also be used in addition to other communication networks to provide redundancy. For example, the cellular network may automatically be used as a fallback if the (primary or preferred) WiFi network fails. When the primary or preferred Wifi network becomes available, communications may automatically re-connect to the primary or preferred network.

Figure 3:
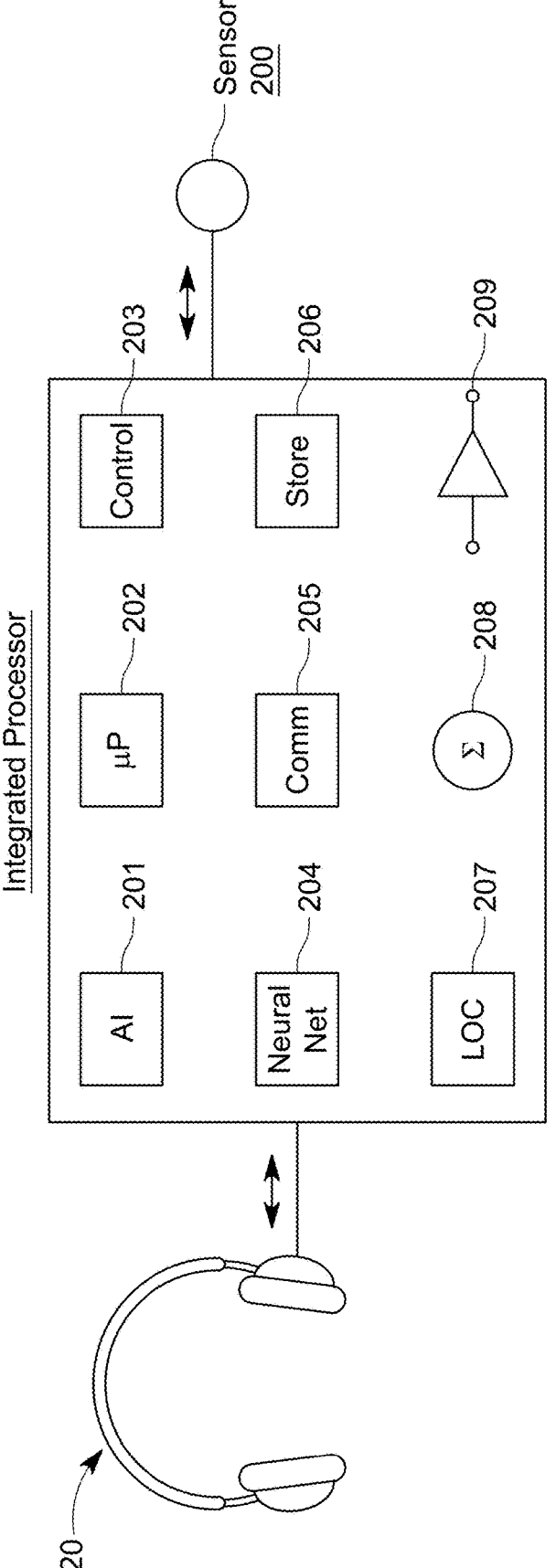
FIG. 3 is a diagram illustrating an exemplary system that includes the headset containing an integrated processing unit, controller, memory for locally executing computer programs for communication, receiving sensor data, and performing signal processing according to an embodiment of the subject matter described herein.

FIG. 3 is a diagram illustrating an exemplary system that includes the headset containing an integrated processing unit, controller, memory for locally executing computer programs for communication, receiving sensor data, and performing signal processing according to an embodiment of the subject matter described herein. Referring to FIG. 3, the headset 20 may contain various additional component, modules, or devices for implementing the functionality described herein. These additional components may include artificial intelligence (AI) 201 including a machine learning (ML) processor 201, machine to machine M2M technologies, an integrated micro processing unit 202, controller 203, memory 206, computer programs 201, communication 205, location devices 207, signal processing components 208, and analog and/or digital electronics 209. The location devices 207 can include, for example, GPS, Assisted GPS, triangularization, beacon, indoor tracking, accelerometers, dead reckoning, and/or accelerometer devices for tracking and location. This allows notifications to the administrator if the subject wanders or begins to wander out of a specific boundary. U.S. Pat. No. 7,034,695 entitled "Large area position/proximity correction device with alarms using (D)GPS technology" and U.S. Pat. No. 7,848,905 entitled "Methods, systems, and computer program products for locating and tracking objects" are each incorporated by reference herein.

The headset 20 may also contain or be communicatively coupled with a sensor 200, such as a microphone for gathering audio data. The audio data gathered by sensor 200 may include both the voice of the user as well as environmental sounds from a source other than the user. The integrated processor in FIG. 3 may receive input from the sensors 200 using one or more communications links, methods, protocols, or transmission media including wired or wireless communications.

The computer programs 201 can be configured for tasks such as sensory input data processing including filtering or conditioning the sensory input data and analyzing the sensory input data for trends. The computer programs 201 may utilize artificial intelligence, real intelligence, neural networks, Bayesian statistical methods, machine learning, reinforcement learning, fuzzy logic, genetic controllers, regular control systems, and adaptive controllers as an example.

The following information, for example, may be measured for trends: Heart Rate, intervals between heartbeats (irregularity indicates stress, constant indicates calm), blood pressure, body temperature, movement/steps per minute/hour/day, noises coming from the subject, calories burned, calories consumed sleep cycles and statistics, heart rate during sleep, game performance and reward and responses to track such as contentment, ability to focus, anxiety, and a plurality of moods across days, weeks, etc., and EEG brain wave monitoring.

Figure 4:
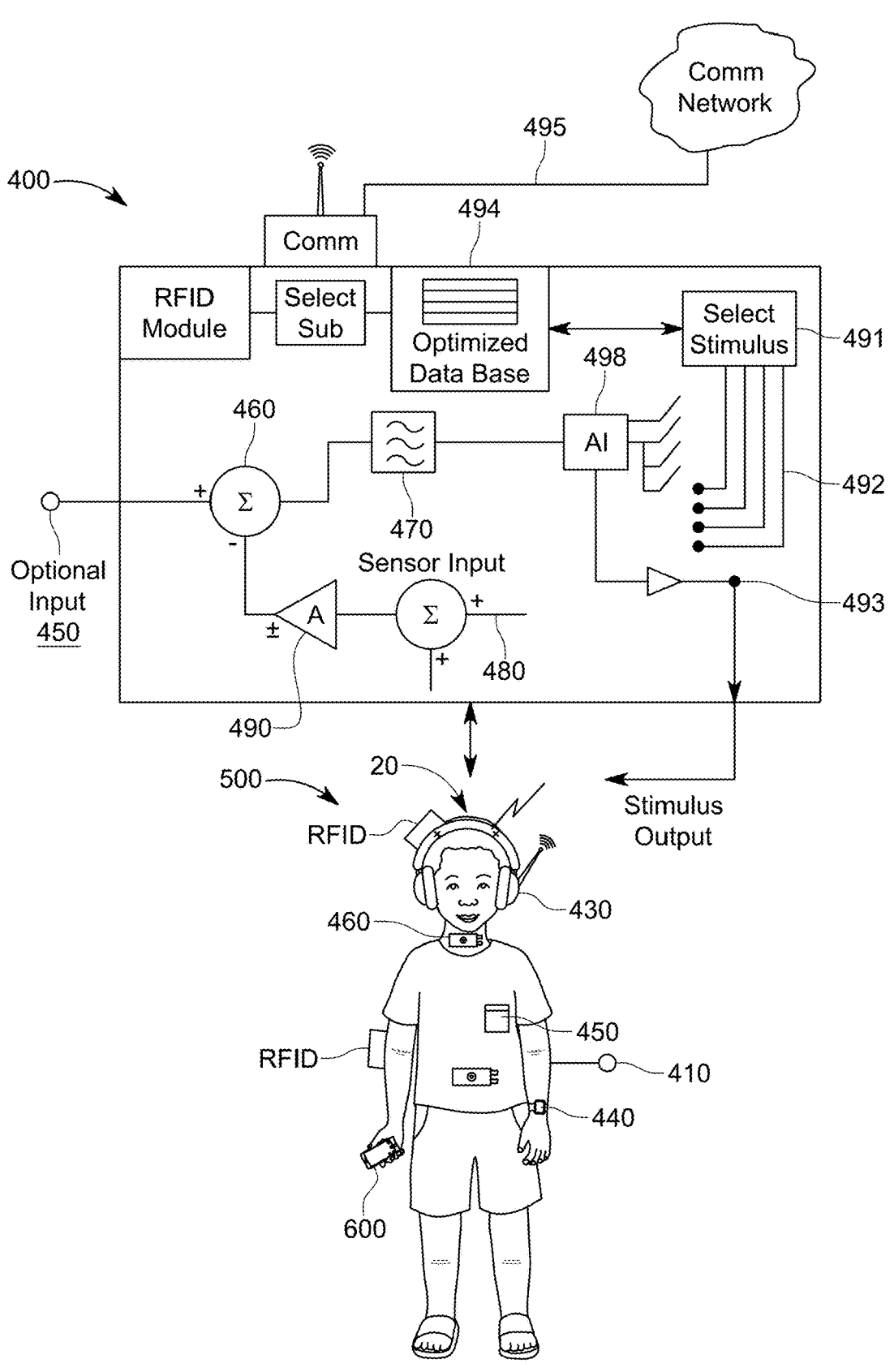
FIG. 4 is a diagram illustrating an exemplary system that includes a pair of linked RFID devices, with one located on the user and another located in the headset, for uniquely and automatically identifying and associating a user with the headset according to an embodiment of the subject matter described herein.

FIG. 4 is a diagram illustrating an exemplary system that includes a pair of linked RFID devices, with one located on the user and another located in the headset or responsory device, for uniquely and automatically identifying and associating a user with the appropriate device or headset according to an embodiment of the subject matter described herein. Referring to FIG. 4, input data from the sensors are fed into the inputs 450 and 480 of the controller 400. Once received by the controller 400, the data is collected by collector 460 and collector 480. Collector 460 may receive optional input 450 and collector 480 may receive input collected by sensors on the user. These inputs are then conditioned at conditioning modules 470 and 490. These collectors and conditioners may be summing devices, filters, amplifiers, signal conditioners and could contain weighting of the signals at this front end.

The conditioned input data is then provided to AI module 498 for selecting a stimulus output 491 to be provided to the user. This selection is based on the user profile and sensor input data, which is refined and optimized by means of learning algorithms described herein. The refining and optimizing of which stimulus should be provided to the user, given the input data may be performed in learning mode and/or continuously while in operational mode. The input data is correlated to output data in either an AI supervised or un-supervised manner.

The AI module 498 may be used in conjunction with a database 494. Database 494 may store information associating one or more sensory input values, or ranges of values, with one or more actions (supervised or unsupervised) to be taken. Additionally, database 494 may store sensory input data for multiple users and/or historical data over a period of time. In one embodiment, AI module 498 may be a look up table which a selection of response 492 is based on experience. Database 494 may reside locally, on the wearable device, in the cloud, or a combination of these storage machines.

After an action (e.g., stimulus) is selected, the action may be performed or otherwise implemented. For example, the action may include providing instructions to the headphones 493 to output audio, such as a calming voice or music, to a haptic device for providing massage or vibration, or to an electric shock device for providing an electric shock to the user; especially if it is an animal such as a dog or livestock. Although sensory Electrical therapy with different levels of intensity on different parts of the body was more popular at the turn of the century for humans, it is contemplated that these sorts or treatments may still have some level of usefulness. However, it is more likely these techniques may be incorporated on animals for behavioral or location/positional correction. For example, a complex system involving AI analysis of a dog could determine the level of stress on the animal and gently offer a vibrational buzz or slight electrical stimulation to head off barking, anxiety attacks or hyperactivity. A smart Thunder shirt could also be controlled and implemented. A learning algorithm along with location data in the analysis could anticipate when the animal is likely to cross a physical boundary and some preemptive action could be implemented as a boundary correction device. Here the AI engine is constantly updating the health and position of the animal determining trends and predicting future locational behavior while selecting the proper stimulus or combination of stimuli for correction.

In any case, after the action has been performed, sensory measurements may continue to be acquired and provided as feedback to the system for analysis. In one example, this analysis includes comparing the current sensory measurements to a history of sensory activity based on previously performance of previous times. This may allow the system to determine whether the effectiveness, or rather estimate a probability that the current action is steady state, increasing, or decreasing as applied to the subject or user. Exemplary methods are through a mathematical analysis of the trends including determining the derivatives and integration of the response. Feedback or feedforward analysis can also be used to determine a change in the response for optimizing the maximum effect of the action on the user's sensory measurements.

The embodiment shows the subject 500 with an RFID device located on the headphones 430 as well as on the subject 500 which can be used for identification. This identification allows for different headphones to be linked with different subjects, as may occur in a classroom setting. Matching a pair of headphones with a subject allows for seamless sharing of headsets among subjects. The identity (e.g., an identifier or ID) of the subject can be used for matching particular parameters, AI models, coefficients and in general the solutions to particular subjects. In FIG. 4, the headset 430 links to the controller 400 which loads the proper models into the headset 430 depending on the identification. These models can be stored on the headsets, the cloud, a LAN or selected in the APP which all could be part of the identification, authorization, authentication, encryption, licensing of the system. The identification may also be based on a machine identifier such as a MAC address, or for example an IP address of the subject's cell phone or other tablet or electronic device.

Figure 5:
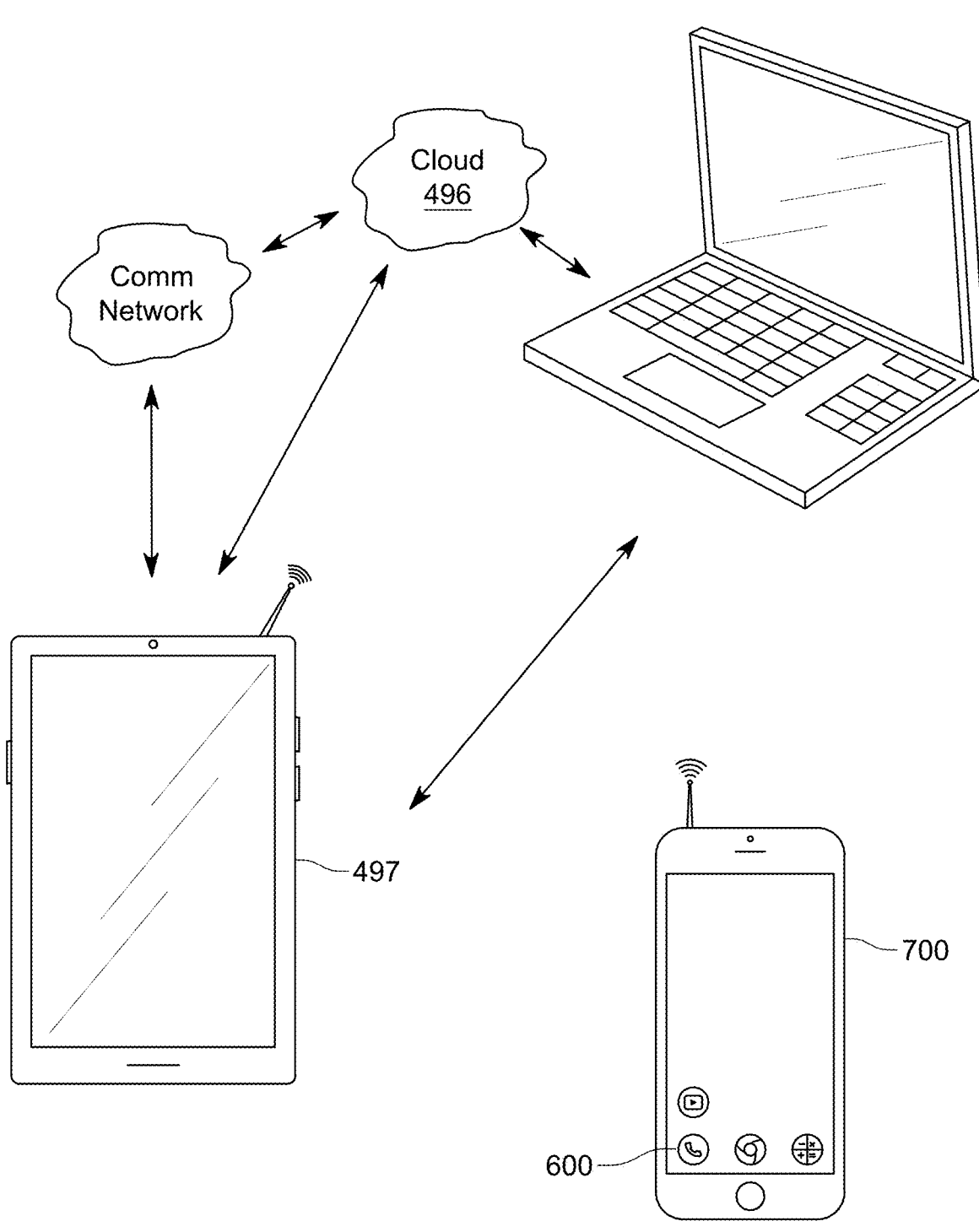
FIG. 5 is a diagram illustrating an exemplary system and communication network for communicating alerts and/or data from the headset to another location, such as the cloud, a phone, a tablet, or a laptop which can perform monitoring, encryption, authentication, security, and control of the headset according to an embodiment of the subject matter described herein.

FIG. 5 is a diagram illustrating an exemplary system that includes a communication network for communicating alerts and/or data from the headset to other locations or machines, such as the cloud, a phone, a tablet, or a laptop which can perform monitoring, encryption, authentication, security, and control of the headset according to an embodiment of the subject matter described herein. Referring to FIG. 5, communication of data from the controller 400 may be made through a communication network 495. Communicated data may include alerts, notifications, or sensory measurements. Data results may be communicated to the cloud 496, a tablet and/or laptop 497, and/or phone 700 associated with a parent, caretaker or guardian of the subject or user 500. Phone 700 may execute software application 600 for performing monitoring, encryption, authentication, security, and control algorithms. It is appreciated that processing and decision making can also be integrated into device 500 and/or device 400, in the cloud 496, or local or remote computational devices 497 and 700. Hence to save power, all processing could be implemented in the cloud 496 and results, notifications, alarms transmitted back to the local devices 700, 497, 500, and 400.

The system disclosed herein may be implemented as a client/server type architecture but may also be implemented using other architectures, such as cloud computing, software as a service model (SaaS), a mainframe/terminal model, a stand-alone computer model, a plurality of non-transitory lines of code on a computer readable medium that can be loaded onto a computer system, a plurality of non-transitory lines of code downloadable to a computer and the like which are within the scope of the disclosure.

The system may be implemented as one or more computing devices that connect to, communicate with and/or exchange data over a link that interact with each other. Each computing device may be a processing unit-based device with sufficient processing power, memory/storage and connectivity/communications capabilities to connect to and interact with the system. For example, each computing device may be an Apple product such as an iPhone or iPad product, a Blackberry like device, a Samsung, Google or Nokia product, a mobile or non-mobile product that executes the Android operating system, a personal computer, a tablet computer, a laptop computer and the like and the system is not limited to operate with any particular computing device. The processing could even be split up among GPUs and CPUs of the same or different machines. The link may be any wired or wireless communications link that allows the one or more computing devices and the system to communicate with each other. In one example, the link may be a combination of wireless digital data networks that connect to the computing devices and the Internet. The system may be implemented as one or more server computers (all located at one geographic location or in disparate locations) that execute a plurality of lines of non-transitory computer code to implement the functions and operations of the system as described herein. Alternatively, the system may be implemented as a hardware unit in which the functions and operations of the back-end system are programmed into a hardware system. In one implementation, the one or more server computers may use Intel® processors, run the Linux operating system, and execute Java, Ruby, Python, C, C++, Regular Expression, Flex 4.0, SQL etc.

In some embodiments, each computing device may further comprise a display and a browser application so that the display can display information generated by the system. The browser application may be a plurality of non-transitory lines of computer code executed by a processing unit of the computing device. Each computing device may also have the usual components of a computing device such as one or more processing units, GPU, memory, permanent storage, wireless/wired communication circuitry, an operating system, etc.

The system may further comprise a server (that may be software based or hardware based) that allows each computing device to connect to and interact with the system such as sending information and receiving information from the computing devices that is executed by one or more processing units. The system may further comprise software- or hardware-based modules and database(s) for processing and storing content associated with the system, metadata generated by the system for each piece of content, user preferences, and the like.

In one embodiment, the system includes one or more processors, server, clients, data storage devices, and non-transitory computer readable instructions that, when executed by a processor, cause a device to perform one or more functions. It is appreciated that the functions described herein may be performed by a single device or may be distributed across multiple devices.

When a user interacts with the system, the user may use a frontend client application. The client application may include a graphical user interface that allows the user to select one or more digital files. The client application may communicate with a backend cloud component using an application programming interface (API) comprising a set of definitions and protocols for building and integrating application software. As used herein, an API is a connection between computers or between computer programs that is a type of software interface, offering a service to other pieces of software. A document or standard that describes how to build or use such a connection or interface is called an API specification. A computer system that meets this standard is said to implement or expose an API. The term API may refer either to the specification or to the implementation.

Software-as-a-service (SaaS) is a software licensing and delivery model in which software is licensed on a subscription basis and is centrally hosted. SaaS is typically accessed by users using a thin client, e.g., via a web browser. SaaS is considered part of the nomenclature of cloud computing.

Many SaaS solutions are based on a multitenant architecture. With this model, a single version of the application, with a single configuration (hardware, network, operating system), is used for all customers ("tenants"). To support scalability, the application is installed on multiple machines (called horizontal scaling). The term "software multitenancy" refers to a software architecture in which a single instance of software runs on a server and serves multiple tenants. Systems designed in such manner are often called shared (in contrast to dedicated or isolated). A tenant is a group of users who share a common access with specific privileges to the software instance. With a multitenant architecture, a software application is designed to provide every tenant a dedicated share of the instance—including its data, configuration, user management, tenant individual functionality and non-functional properties.

The backend cloud component described herein may also be referred to as a SaaS component. One or more tenants which may communicate with the SaaS component via a communications network, such as the Internet. The SaaS component may be logically divided into one or more layers, each layer providing separate functionality and being capable of communicating with one or more other layers.

Cloud storage may store or manage information using a public or private cloud. Cloud storage is a model of computer data storage in which the digital data is stored in logical pools. The physical storage spans multiple servers (sometimes in multiple locations), and the physical environment is typically owned and managed by a hosting company. Cloud storage providers are responsible for keeping the data available and accessible, and the physical environment protected and running. People and/or organizations buy or lease storage capacity from the providers to store user, organization, or application data. Cloud storage services may be accessed through a co-located cloud computing service, a web service API, or by applications that utilize the API.

Figure 6:
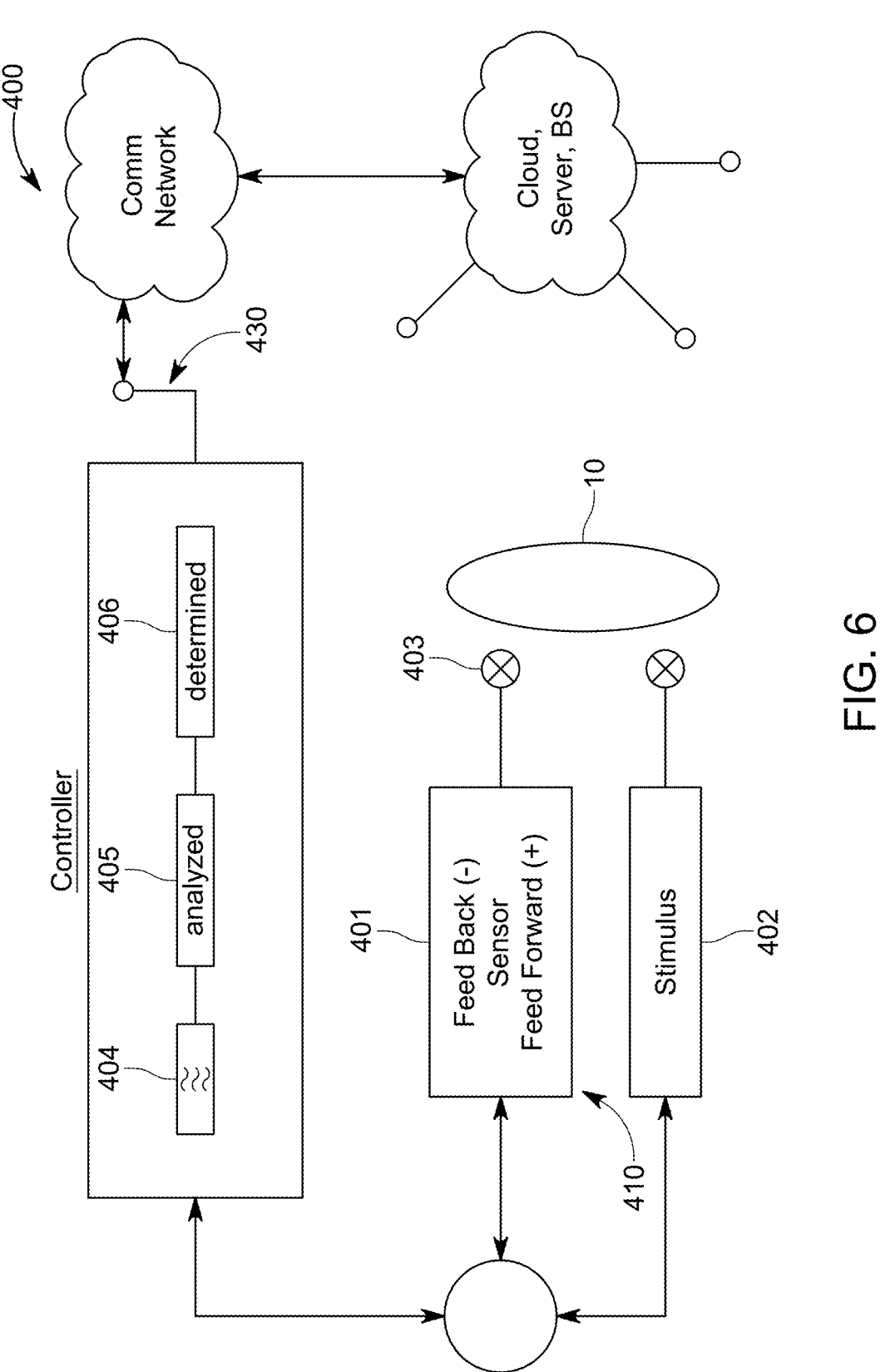
FIG. 6 is a diagram illustrating a simplified network configuration where a controller receives input from sensors attached to the subject according to an embodiment of the subject matter described herein.

FIG. 6 is a diagram illustrating a simplified network configuration where a controller receives input from sensors attached to the subject according to an embodiment of the subject matter described herein. Referring to FIG. 6, controller 400 receives input from the sensors 403 attached to the subject 10. In the embodiment shown, a feedback/feedforward sensor 401 is located between the input received from the sensors 403 and the controller 400.

Information that is fed back to the controller may be conditioned by conditioning module 404, analyzed by analysis module 405, and a response determined by response determination module 406. Here, a stimulus is selected by the controller 400 and provided to the stimulus module 402 for exciting the subject 10 and the sensor 403. Again, the network can communicate with the communication network and the cloud or server for further intelligent analysis data mining, data storage and computation. The sensors can incorporate biological feedback, neurological feedback, and environmental feedback.

Figure 7:
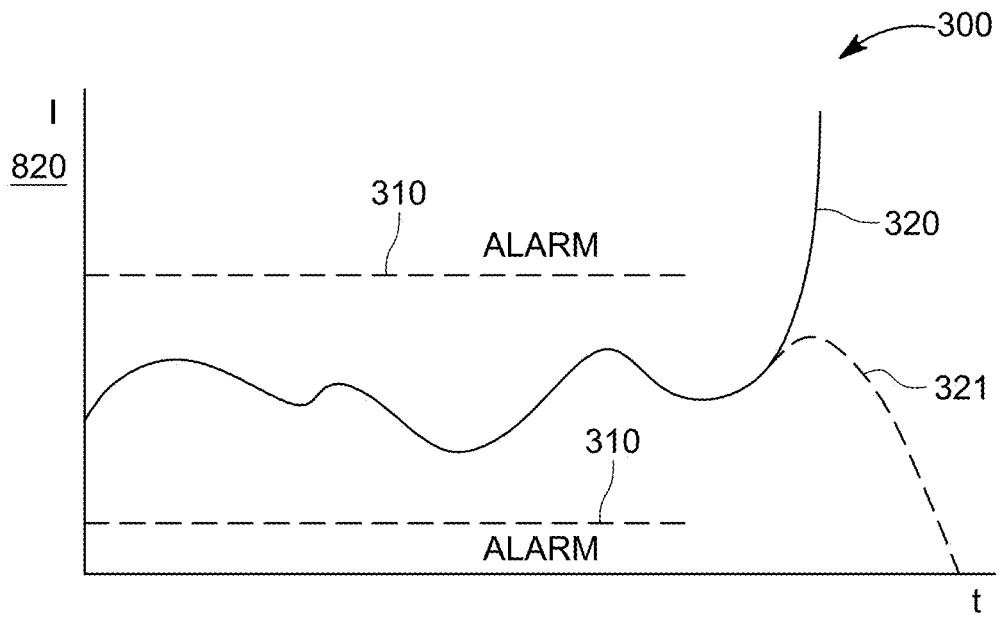
FIG. 7 is a diagram illustrating an exemplary baseline range for a subject and a threshold for generating an alarm when the user is outside of their baseline range according to an embodiment of the subject matter described herein.

FIG. 7 is a diagram illustrating an exemplary baseline range for a subject and a threshold for generating an alarm and/or response when the user is outside of their baseline range according to an embodiment of the subject matter described herein. Referring to FIG. 7, a baseline 300 is shown for a subject. The baseline 300 may include a range of values including an upper threshold value and a lower threshold value. These thresholds may also be referred to as boundaries. When the user is within their baseline range, the user's value is between these thresholds.

As will be described in greater detail with respect to FIG. 8, the user's value 820 indicated on the Y, or vertical, axis may be based on a single intensity output or multiple outputs conditioned outputs from sensory systems. The upper and lower thresholds 310 may be individually tailored or associated with each user and based on experience, knowledge base processing, and learning algorithms. In some embodiments, these thresholds may initially be provided as part of a generic user profile and then revised based on feedback and learning of/from the subject or user.

Each of the thresholds may also be associated with triggering an action. This action may include generating and sending an alarm or notification when the threshold has been crossed or an increasing trend concern. For example, an alarm 310 may be associated with both the upper and lower thresholds such that a parent or guardian is automatically notified when the user's stress level is outside (either above or below) their baseline range. Furthermore, an output response may be implemented automatically, manually, or even physically by the caretaker or subject.

Additionally, a trend of the user's stress level may also trigger a notification before a threshold has been crossed. Here, if the curve 320 starts to accelerate or move towards the upper boundary of the output sensor response, an alarm and action can automatically take place to bring the output 320 back to safe operation conditions representing a safe medical or mental state. Conversely, hypoactivity of the user may cause curve 321 to trend toward the lower threshold indicating an oncoming depressive state 321. Based on an analysis in the time domain, frequency domain, or any mathematical space, the system may determine a likelihood that the user will leave their baseline conditions. Based on this likelihood, early intervention may be possible to prevent the user from leaving their baseline conditions rather than waiting for the user to leave their baseline before responding. The sensitivity of reacting to this likelihood determination may be adjusted based on user preferences to avoid intervening too early or too often (e.g., false alarms).

Figure 8:
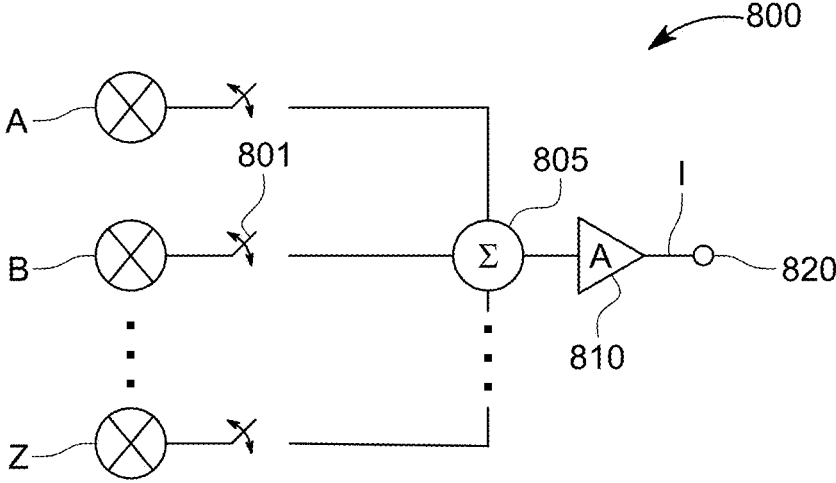
FIG. 8 is a diagram illustrating a sensor network comprising multiple sensors which can be weighted, averaged, filtered, and selected according to an embodiment of the subject matter described herein.

FIG. 8 is a diagram illustrating a sensor networking comprising multiple sensors which can be weighted, averaged, filtered, and selected according to an embodiment of the subject matter described herein. Referring to FIG. 8, the sensor network 800 includes multiple sensors such as temperature, blood O2 level, pulse, rhythm, pressure, EKG, limb movement, fidgeting, jerking, jittering, shaking, uncontrollable movements, motion detectors, accelerometers, etc. These sensors 800 can be activated by software through switches or simultaneously with a multiplexer 801, summed at module 805, conditioned, filtered and amplified at module

810, and set for the next stage of analysis as output data 820. Here, the output data 820 it could be compared to known behavioral patterns for prediction, correction, and control. Many times, the amplifier 810 is on the input side of the summing device for each channel, and weighting can also be applied before of after 801 or 820 for that matter.

The output of FIG. 8 may then be used to determine which actions, if any, should be performed. This process may include using tables, such as those in FIGS. 9 and 10, to look up associated responses depending on the data. Thus, in some embodiments, the system (e.g., algorithm, autonomous selection, manual operation) may use a table look up, as in FIG. 10, where a sensor (or a combination of sensory inputs) is associated with actions including: playing a familiar voice or phrase, music selection, a haptic massage, with sounds, volumes, or videos. The user is monitored, and the feedback is used for improving the effectiveness in the selected action for achieving a change in the user's measured stress levels.

Figures 9, 10, 11:
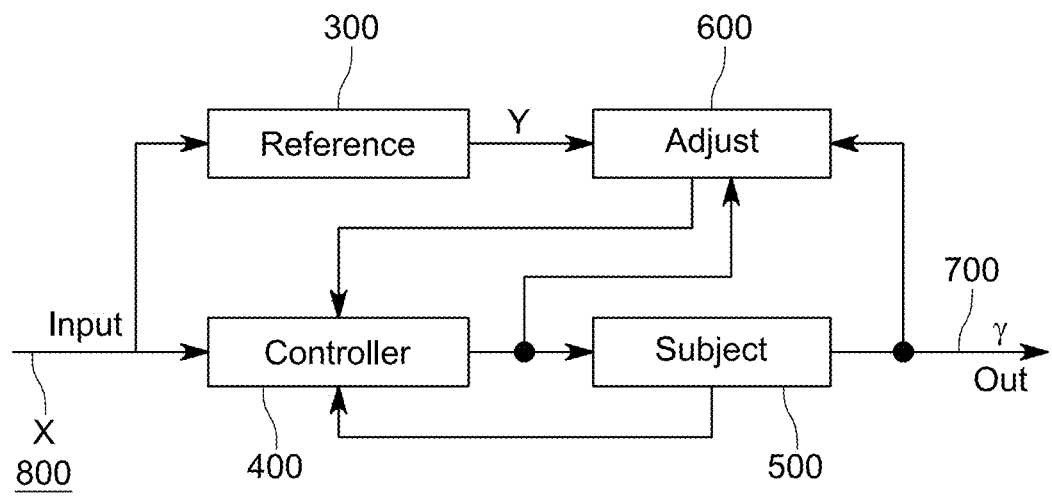
FIG. 9 is a diagram illustrating an exemplary lookup table for determining a mode of operation, such as autonomous or manual, for a given sensor input according to an embodiment of the subject matter described herein.
FIG. 10 is a diagram illustrating an exemplary lookup table that associates sensors with one or more data fields associated with actions to be performed for calming the subject according to an embodiment of the subject matter described herein.
FIG. 11 is a diagram illustrating a reference based adaptive controller where the input from the sensors is compared to the reference and routed to the controller according to an embodiment of the subject matter described herein.

FIG. 9 is a diagram illustrating an exemplary lookup table for determining a mode of operation, such as autonomous or manual, for a given sensor input according to an embodiment of the subject matter described herein. Referring to FIG. 9, three types of methods are listed for determining an action associated with sensor data. The first method includes using a table that associates sensor data with actions. The second method includes allowing or requiring the user, such as the user or a parent or guardian, to manually select an action. This may include a user interface (e.g., button) that the user may use on a phone or similar device to select the action to be performed. It could also be a physical response such as notifying the caretaker to put a blanket on a child or patient. The third method includes autonomous determination of the action based on the sensor data. This allows for AI or ML algorithms to determine the action based on more complicated or different models than the table lookup of the first method. Each method may have advantages and disadvantages, such as computational requirements. Thus, one method may be selected to be used and this selection may be changed by the user. Here, the Table method is selected, and the manual and autonomous methods are indicated as Selections. Hybrid approaches are also possible.

FIG. 10 is a diagram illustrating an exemplary lookup table that associates sensors with one or more data fields associated with actions to be performed for calming the subject according to an embodiment of the subject matter described herein. Referring to FIG. 10, three sensors are each associated with three data fields labeled as: selection, output, and feedback. Sensor A is associated with a familiar voice phrase selection, sound output, and improving feedback. In other words, an audio clip of a voice that is familiar to the user may be played in the user's headphones and monitored to see whether it improves their stress level. Sensor B is associated with a music selection, volume output, and increasing feedback. In other words, a song may be played in the user's headphones starting at a lower volume and increasing over time. Sensor Z is associated with a haptic massage selection, intensity output, and decreasing feedback. In other words, a massage device on the user may massage the user at a higher intensity initially and decreasing over time as the user's stress level decreases. Again, hybrid and combinations of sensors and outputs can be weighted for their use in selection, intensity, frequency and the like.

FIG. 11 is a diagram illustrating a reference based adaptive controller where the input from the sensors is compared to the reference and routed to the controller according to an embodiment of the subject matter described herein. Referring to FIG. 11, the input 800 from the sensors is compared to reference 300 and routed to controller 400. The comparison is adjusted manually, or automatically, by adjustment module 600 which is in communication with the controller 400 that outputs to the subject 500 through a chosen medium such as headphones, heads up display, glasses, weighted blanket, and the like. This response is measured and fed back to the controller from the subject 500 to the controller 400. Although this could be coupled to an AI engine, it could also run on its own with a simple system of just a few channels. The channels referring to a few inputs and a few outputs. For instance, if it was a single input and single output device, the input 800 could be compared 300 and gain adjusted 600 for an initial start, and adaptively reduced as the stress precursor improves. Here, the input is simply a sensor such as temperature or a cardiovascular measurement. The adaptive controller would compare 300 the input to a reference and activate a massaging device when a threshold close to some predetermined value. Here, the gain of the system could start high, indicating more power to the massage, and as the subject's precursor began to decrease the controller could adjust 600 and soften the response accordingly.

Figure 12:
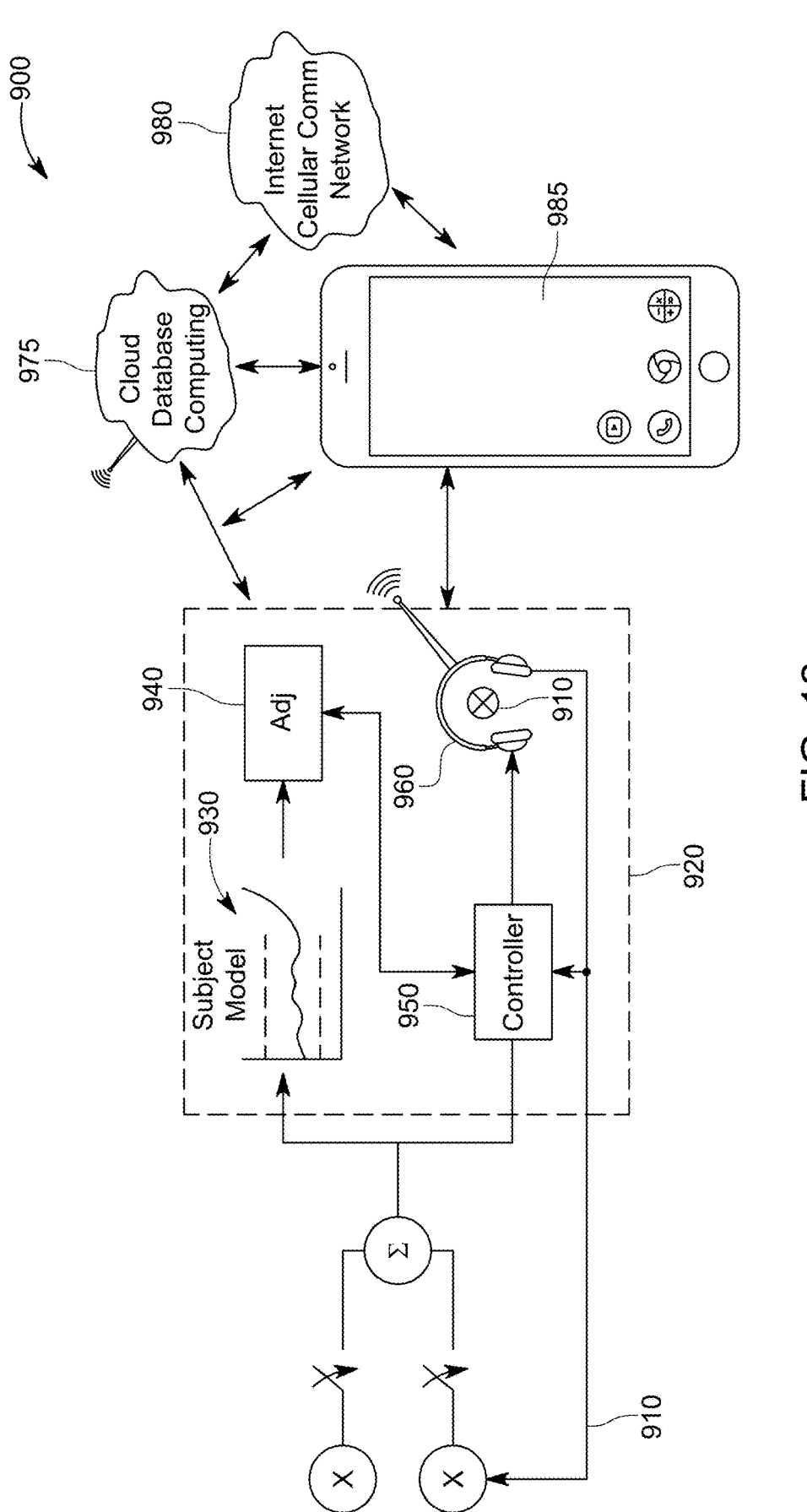
FIG. 12 is a diagram illustrating an exemplary system where one or more sensors are activated, summed, conditioned, and input into a system comprising a controller, a subject baseline model, an adjustment module, and headphones according to an embodiment of the subject matter described herein.

FIG. 12 is a diagram illustrating an exemplary system where one or more sensors are activated, summed, conditioned, and input into a system comprising a controller, a subject baseline model, an adjustment module, and a wearable reactionary device such as headphones according to an embodiment of the subject matter described herein. Referring to FIG. 12, diagram 900 shows how the sensors 910 are activated, summed, conditioned and input into the system 920. The system 920 includes controller 950, subject base line model 930, adjustment module 940, and headphones system 960. Headphones system 960 has sensors 910 attached to, or in communication with, the subject. The sensor inputs are processed and compared to the subject model 930 in preparation for adjustment outputs 940. The subject model 930 in the embodiment shown is a priori and is used in a comparison mode or a learning mode as further explained.

Alternatively, artificial intelligence, machine learning can also be used over time to improve or suggest model parameters. These parameters are used mathematically based on a learning history to determine Neural Network models and optimize and improve the response of a particular subject. The adjustment algorithm can apply an optimized equation of coefficients describing the multi-input, weighted, and/or multi-dimensional output response.

As a result, singular stimuli as well as singular inputs are not the only basis for determining actions to be performed for calming the subject. For example, it may require a combination of input sensors to determine a combination of output responses such as a favorite tune, voice, and a haptic output signal to lower (or raise) the excitation level of the subject, as defined by 820 of FIG. 7.

The previous Figures and discussion incorporate Artificial Intelligence, Machine Learning and Deep Learning concepts for implementation of the prediction and response of this invention.

Figure 13:
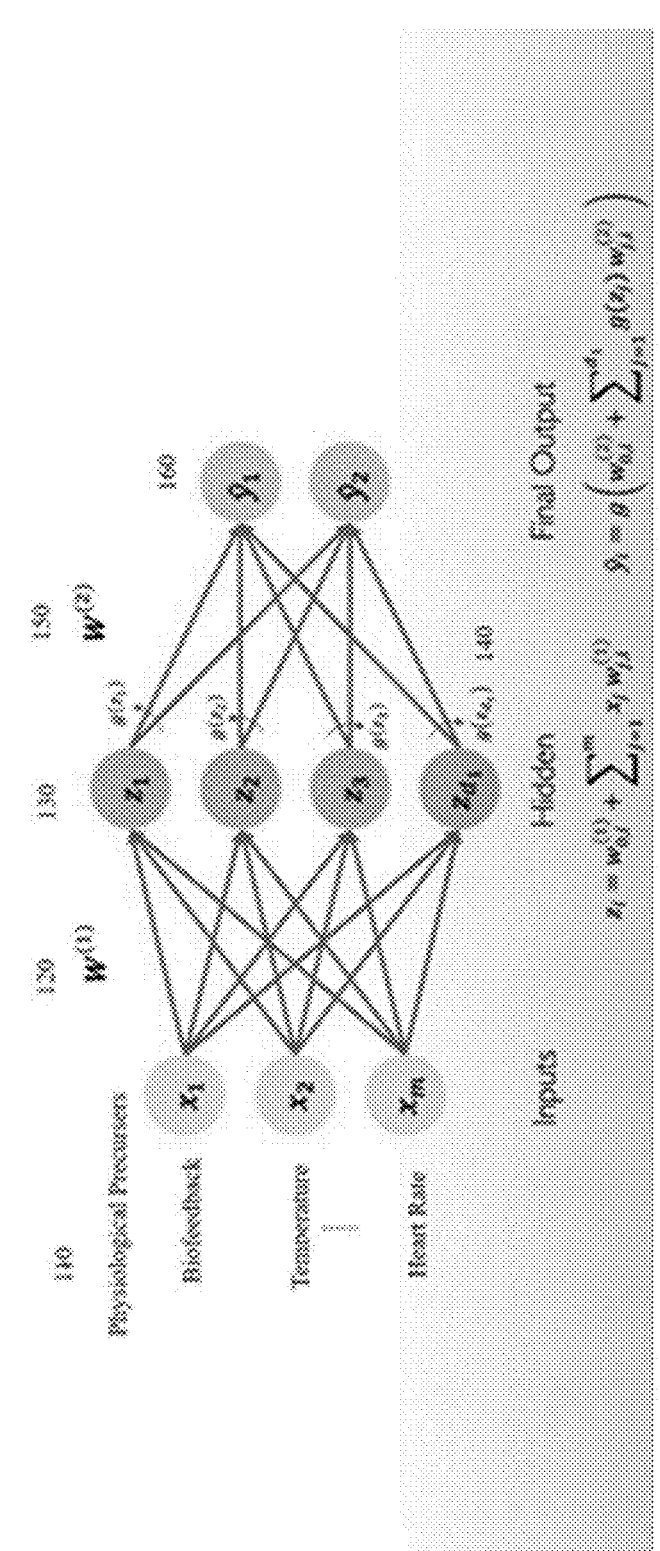
FIG. 13 shows a single layer Neural Network (NN) suitable for predicting and preventing negative behaviors according to an embodiment of the subject matter described herein.

FIG. 13 shows a single layer Neural Network (NN). The sensor input features, or input vectors are represented by x and are weighted and summed into the hidden layers z where a nonlinearity g(z) is applied for the output y. For the calming device, the input vectors are the outputs or measurements from the numerous sensory sensors of the subject desired for control. For a calming device, the inputs could be signal measurements representing the subjects heart rate, temperature heart rhythm, measured audio, muscle spasms, O2, jerking-jittery motions, controllable or uncontrollable actions, and the many physiological precursors and biofeedback sensors mentioned in previous description. If the subject begins to show signs of stress (or pleasure), the measured values are individually represented by the vector x. The input vectors are then weighted $W^1$ summed and applied to a nonlinear activation function such as a rectified linear unit, leaky rectified linear unit, sigmoid, tanh, ReLU, LReLU, ELU, GeLU or a step function to name a few. Custom nonlinearities are also applicable as there are many examples of nonlinear activation functions. Here the g(z) functions are shown summing to two outputs and in this case weighted again with $W^2$. Although a single Neural Network is shown indicated in FIG. 13, many stacks of hidden layers z are used in deep learning approaches. The output y can be a single vector or consist of multiple vectors. Shown are two outputs.

Many software packages use languages that contain open-source code for implementation of the matrix calculations. Some, like TensorFlow™, Keras™, PyTorch™, Scikit-Learn, ONNX™ can be used in languages such as C or Python. Other programs are also available in packages such as Matlab™ and DLPY from SAS™.

Using NN, the system can process the inputs, learn, model, and recognize hidden patterns of behavior originating in the raw input data x. These patterns are classified, correlated, and labeled in a behavioral space which can be represented in a time (or other dimension such as frequency) sequence. With this sequence, predictions of future states are determined, and the computational output is used to select the optimum response necessary to change the behavior of the subject. New inputs are measured, and the process again is fed into the NN model to gauge the resulting response. For example, if the inner ear temperature is increasing, and the heart rate is ascending, the NN output y is used to classify or label the subject with an increasing stress level. If this stress level begins to approach a boundary as determined by the NN model, the system activates a response to the subject such as calming music, a vibration, visual stimulation such as darkening sunglasses, and continues to monitor the inputs. An alert is also sent to the parent, teacher, a central operator, or guardian. In other situations, the subject may need excitation desirous to increase heart rate, breathing, and temperature for example. Here the increase of physiological precursors may be based on biofeedback and the data fusion of the many possible inputs through the NN is incorporated. Hence, the data x is determined, fed into the NN, the output classified and mapped to the behavioral space. Through the training sessions, the boundaries and targets are thus predetermined for increasing subject stimulus. The output y is mapped to this space and a decision is made to hold or to activate/increase one or more stimuli. The process is repeated until, there is enough data to be analyzed trained and adjusted to the desired effects.

The temporal changes in patterns of behavior can also be captured by time dependent machine learning models that capture the inherent relationship between patterns of behavior at different times. These models are able to store multiple previous states and are commonly used in language translation, synthetic image generation as well as human interaction using robots. Examples of such models include Long Short-Term Memory Networks, Recurrent Neural Networks, as well as Transformers.

Additionally, the sensor input could be pre-processed to handle failure, erroneous measurements, or loss of communication with the main computing unit that performs the prediction operation. Furthermore, to reduce the computational complexity and increase the performance of the neural network, the sensor data may be pre-processed. Such pre-processing include extraction, data cleaning, point wise non linearities, such as log amplitude for sounds, but may also include the use of embeddings.

The stimulus device could take on many approaches, such as smart headphones to play music, recorded messages, noise cancelling devices, haptic, tactile, massaging such as foot or neck, vibration devices, rocking motions such as in a smart bed, chair, or crib, dimming of lights, electrical stimulation, and mechanical stimulation to name a few. Wi-Fi enabled devices such as Alexa™ could participate and even control these individual responses; or they could be controlled directly by the stimulus device. The processing of data could be on the device, a mobile computer such as a smartphone or tablet, through Alexa™, a LAN, or in the cloud. In other words, the control could be local, remote, by wire, and preferably autonomous; but manual control by these methods is also a viable alternative. Multiple controllers at same or different locations could also participate monitoring, supervising, tweaking, domineering, manipulating, and controlling single or multiple subjects.

Sharing of network models, including types of sensors, classification of the subject's behavior, and response behavioral mapping can be uploaded to the cloud by many users. These models could decrease training efforts and make for efficient starting points for different unrelated subjects. It also leads to deep learning techniques, with many NN layers, memory tracking, embedding, improving classification, pattern recognizing forecasting the intended stimulus response. The subjects' own models and data could be passed to the cloud for intelligent optimization using class similar comparisons. Hence the cloud database would significantly aid the learning of complicated patterns of behavior, pattern recognition, automatically diagnose and translate the subject's behavior and social interaction.

Neural Network and Deep Learning Training:

An example of the learning process could begin with the user attaching the stimulus device and the connected application begins receiving and recording the input-output data. The user observes the data as it is being stored. At the first onset of stress, the data is marked and flagged by the user. The user then selects manually, or additionally from a suggested list or new, an output response, or several responses and the input data is observed to converge or diverge from the desired state. When the proper selection of responses is found, this is recorded and labeled for that input. This is repeated many times for multiple inputs and outputs. After a good collection of data sets and responses is determined and recorded, e.g., 10-30 data points, the system optimization begins. This is performed computationally by the system, and the user need not be concerned with the algorithm. This process involves optimal techniques to minimize a loss function with or without constrains. An example of such technique is curve fitting of the predicted response and the output response or other linear programming.

The output in this case is the vector y where each vector coefficient represents a particular channel with an amplitude. For example, $y_1(a_1, b_1)$, a multidimensional output (other vectors such as multidimensional inputs $x(a_1, b_1)$ are also contemplated) would represent vibration stimuli with coefficients $a_1$ and $b_1$ representing an amplitude and frequency of a vibration and designated by a number. $y_2(a_2)$ could represent music or a recording with $a_2$ representing a volume of a particular song or message and designated by a number representing that volume. $y_3(a_3)$ would represent the dimming of a particular lamp with $a_3$ representing the lumen intensity and color of a smart lamp. The brightness represented and designated by a number. The analog amplitudes of the stimuli or inputs could also be binned into amplitude ranges, and each range could be one-hot encoded. For example, stimulus $a_1$ could be binned into four ranges [0, 100], [100, 200], [200, 500], [500, infinity], the value of 300, would then be represented by the binary vector [0, 0, 1, 0], while the value 1 would be represented by a binary vector [1, 0, 0, 0]. Additionally categorical information such as voice of mother, voice of father, section of a particular song would also be represented using the one-hot encoding.

In another example, the output is the vector y where each vector represents a particular channel with a probability related to amplitude of the vibration. For example, coefficient $y_2$ would represent similar vibration stimuli of a different frequency and a probability of amplitude of vibration and if there are 10 channels of vibration, each probability represents a different setting. Then, $y_{11}$ up to $y_n$, would represent many audio channels such as music or personal recordings each vector coefficient representing a different volume of a particular song or message and designated by a number representing that volume and $y_{n+1}$ would then be the representation of the dimming of a particular lamp, with representations of the lumen intensity and color of a smart lamp. The brightness may be represented and designated by a number or probability.

The algorithm then formulates a loss function between the predicted values and the actual values. In one embodiment, this may include a method of least squares minimizing the difference between the predicted output channel and actual desired output value. During the optimization or training process, the second half of the data is not incorporated in the fitting routine. This secondary data can be used as test data to observe the convergence of the optimization routine and determine if more training or less training data is required. This testing data is input to the system to observe the progress and ensure the fitting is ideal and does not underfit or overfit the data. This is also a small part of what is known as a regularization technique.

The Loss function is used to minimize uses the weights w and the input x to compare to the known output y. Here the Error J is represented as $$\Sigma Loss(f(x^i, w^i), y^i)$$

where $f(x^i, w^i)$ is the predicted value and $y^i$ here is the desired actual value. The system adjusts $w^{(i)}$ for the best fit. Using TensorFlow™ one function is the softmax cross entropy algorithm for example. Another might be a least squares approach. At any rate, in the error space, the algorithm could incorporate techniques such as back calculation gradient or a gradient decent method to find the weighting coefficients that minimize the error. When you have multiple layers of Neural Networks, the loss function incorporates $w^1 \ldots w^2 \ldots$ by means of partial differential equations with respect to the outputs and inputs of the NN for example. This may be handled using programs like TensorFlow™. Adaptive gradient descents are useful when the weighting space has many saddle points and generally represents a complex surface. Exemplary algorithms may include algorithms such as SGD, Adam, Adadelta, Adagrad, RMSProp.

Figure 14:
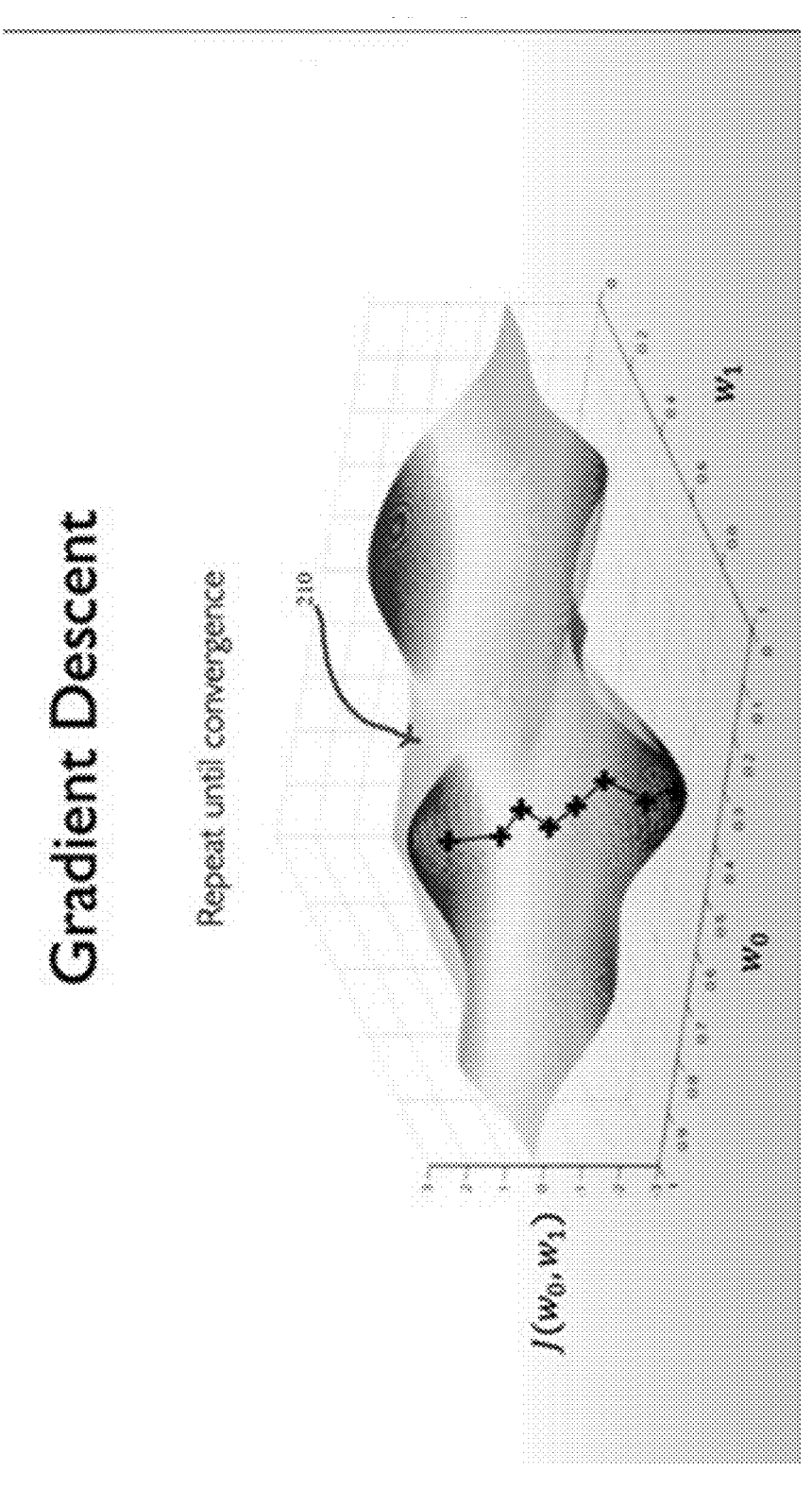
FIG. 14 is example of optimizing the weighting vectors showing a visualizing a simple NN optimization process in error space $J(w^0, w^1)$ according to an embodiment of the subject matter described herein.

FIG. 14 visualizes a simple NN optimization process in error space $J(w^0, w^1)$. Here, behind the scenes the optimum weighting vectors $w^{(i)}$ are found that minimize the error function. Adaptive optimization aids in selecting the right path of minimization and reduces the probability of landing in a saddle point as shown in location 210.

Once the NN model is first optimized it can be turned on for testing and additional data collection. This experience leads to improved training and fine tuning of the system.

Once a model has been trained over a large number of users, supervised transfer learning techniques can be the models to improve the outcome and speed of treatment to a new subject or a new set of subjects. This technique can also be applied when new outputs can be applied. For example, new outputs that can be applied can include the ability to play a new type of music track or new type of stimulus. These transfer learning techniques retrains the last few layers of the neural network and converge fast with a reduced amount of training and testing data.

Figure 15:
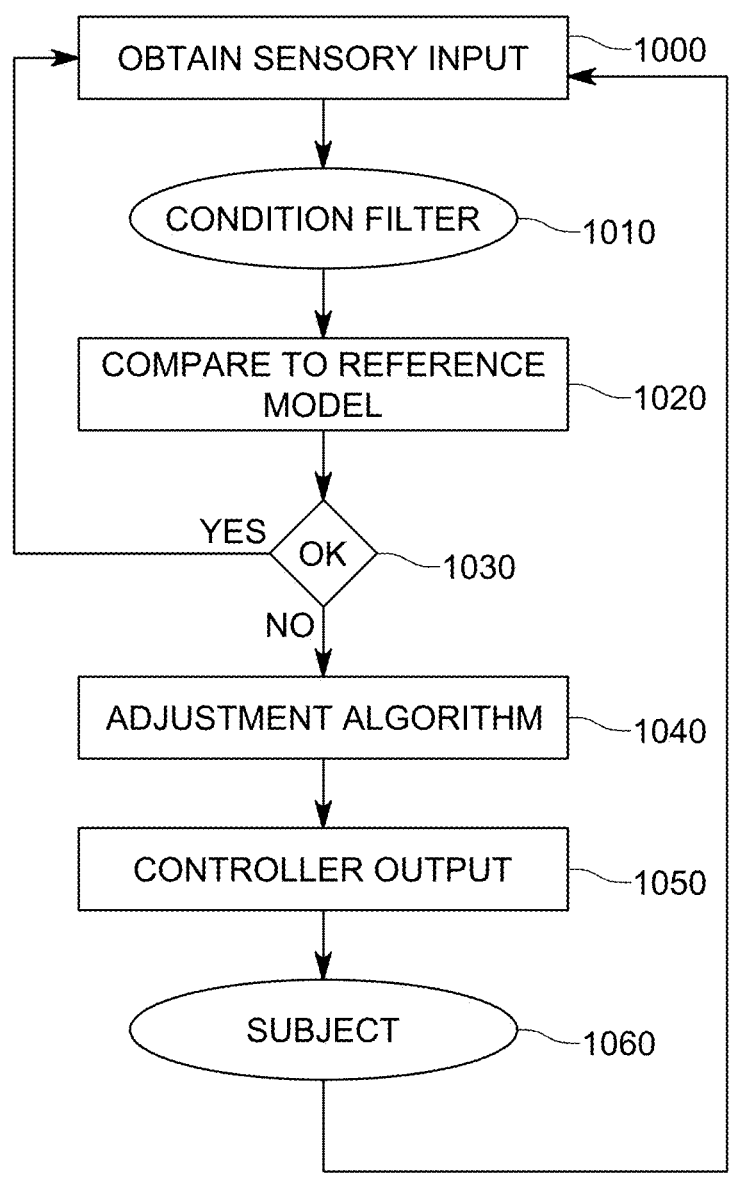
FIG. 15 is a flow chart illustrating exemplary steps for predicting and preventing negative behaviors according to an embodiment of the subject matter described herein.

FIG. 15 is a flow chart illustrating exemplary steps for predicting and preventing negative behaviors according to an embodiment of the subject matter described herein. Referring to FIG. 15, at step 1000 sensory input is obtained.

At step 1010, the sensory input is conditioned and/or filtered. This may include electronic filtering, transformation, amplification, and/or digital conversion.

At step 1020, the conditioned/filtered sensory input is compared to a reference model. For example, a baseline or a user profile associated with the user.

At step 1030, it is determined whether the sensory input is within acceptable tolerances indicated by the reference model based on the comparison in step 1020. For example, a baseline resting heartrate for the user may be between 70 and 75 bpm, as indicated in their personal user profile. The sensory input from step 1010 may be a resting heartrate of 72 bpm. The determination of step 1030 is that the user's resting heartrate is within their normal baseline range. In response to determining that the sensory input is within acceptable tolerances indicated by the reference model, the process may return to step 1000 where sensory input is again obtained for subsequent comparison.

If, however, the sensory input is outside of acceptable tolerances indicated by the reference model, the process may proceed to an adjustment step 1040. For example, if the sensory input from step 1010 indicates a current heartrate of 100 bpm, the user's stress level may be elevated, and action may be taken to reduce their stress levels. If action is to be considered, the sensors comparison is sent to the adjustment algorithm, which could incorporate a parent or guardian on their phone app hot button or could be an intelligent adaptive control program that automatically selects a response based on the sensor type, category, and output, which is sent to the controller for outputting the response to the subject.

At step 1040, an action to be taken is determined. This may include adjusting one or more devices, such as increasing or decreasing the performance or sensitivity of various sensory-mediating devices worn by the user. For example, continuing the example scenario above, the adjustment algorithm 1040 may determine that playing a particular song at a particular volume via the user's headphones should result in lowering the user's heartrate by 28 bpm.

At step 1050, the action determined at step 1040 may be implemented. This may include providing instructions or other data to a controller. For example, a signal may be provided to the user's headphone indicating the music file and a volume level to be played.

At step 1060, the subject receives the output of the controller. For example, the user may hear the music file being played in their headphones. The sensors may continue to be monitored to see if the output is damping out or becoming worse. If damping out, the response output to the subject may stay on course. If, however, things are getting worse the intelligent algorithm from learned responses may change the output, send a different set of commands to the controller until the behavior is modified and controlled. Although this simple example discusses one input, heartrate, multiple inputs are typical and a combination of different outputs could be necessary to obtain the physiological target objective.

Figure 16:
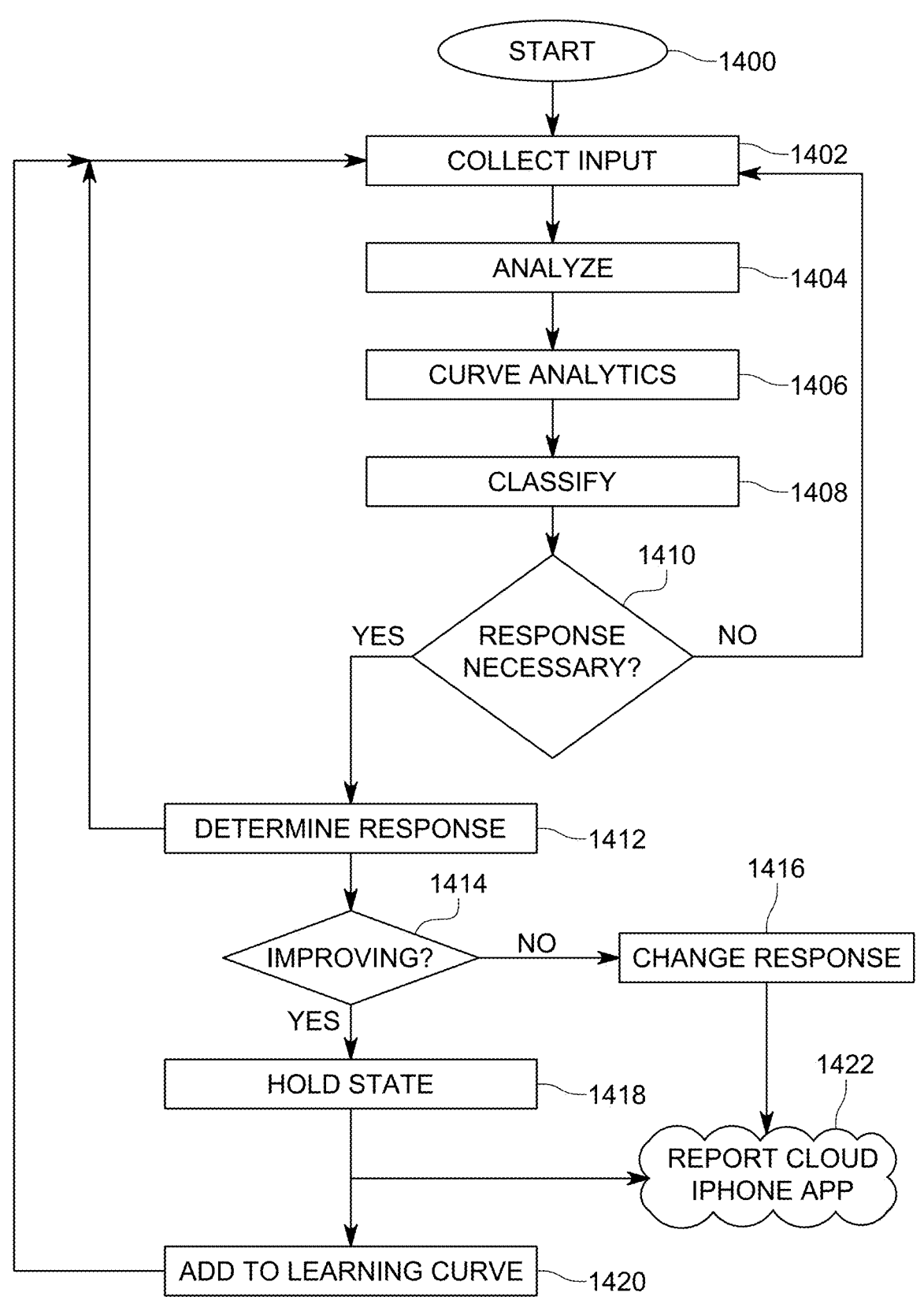
FIG. 16 is a flow chart illustrating exemplary steps for predicting and preventing negative behaviors according to an embodiment of the subject matter described herein.

FIG. 16 is a flow chart illustrating exemplary steps for predicting and preventing negative behaviors according to an embodiment of the subject matter described herein. Referring to FIG. 14, the process begins at step 1400 and proceeds to step 1402 where input is collected. For example, the heartrate of the user is measured. At step 1404, this input is analyzed. For example, a device integrated within headphones of the user, or using a connected mobile phone, the user's heartrate may be compared with a baseline range. At step 1406, analytics are performed where it may be determined whether the user's heartrate is increasing or decreasing over time, and how quickly. At step 1408, this analysis is classified as, for example, within the normal baseline range of the user or abnormal for the user (e.g., elevated). Of course, classification could also involve the choice of different approaches to or types of AI and algorithms.

At step 1410, it is determined whether a response is necessary. For example, if the user's heartrate is within a normal range, indicating the user is not stressed, no intervention response may be required, and the process returns to step 1402 where input is collected again. Alternatively, if the user's heartrate is not within a normal range, indicating the user is stressed, a response may be determined at step 1412. For example, calming music may be played for the user to lower their heartrate.

At step 1414, it is determined whether the response from step 1412 is improving the stress of the user, as measured by their heart rate for example. If the response does not improve the user's stress level, the response may be changed at step 1416. For example, a different piece of music may be played for the user, or a haptic feedback "thunder shirt" may be activated to calm the user. Alternatively, if the response does improve the user's stress level, a hold state is activated at step 1418 where the response is not changed while the user's stress level improves. Responses that are effective in improving the user's stress level are then added to a learning curve at step 1410 for future use. Both responses that are changed because they are ineffective and responses that are held because they are effective may be reported to another device, such as the cloud of an iPhone app, for analysis at step 1422.

Figure 17:
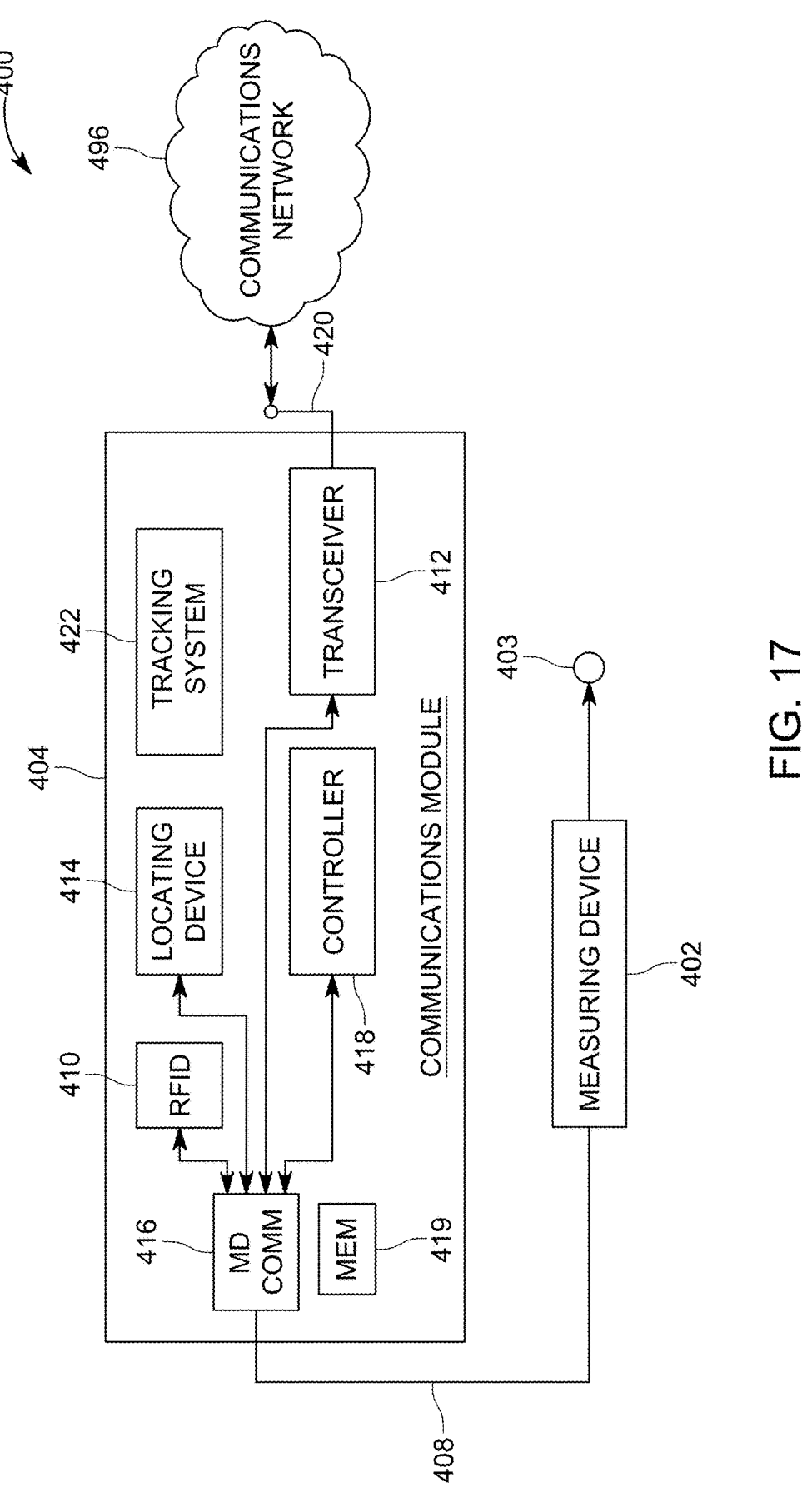
FIG. 17 is a block diagram of an exemplary measuring/locating/tracking system according to an embodiment of the subject matter described herein.

FIG. 17 is a block diagram of an exemplary measuring/locating/tracking system according to an embodiment of the subject matter described herein. Referring to FIG. 15, system 400 can include a measuring device 402 configured to measure one or more properties or characteristics of the user. System 400 can also include a communications module 404 configured to communicate with network-enabled devices. Communications module 404 and measuring device 402 can communicate via a communication element 408 wirelessly through Bluetooth, BLE, an electronic leash, or with any short-range RF connection to the communications module or nearby electronics (shown in this example as a wire, or a trace on a PC board). Although the illustration indicates a hard connection, wireless connections may be received at antenna 420 and routed to the module 416. In parallel with measuring device 402 may be a response device 430 that also communicates with communications module 404.

Communications module 404 can include combinations of an RFID module 410, a transceiver 412, a locating device 414, a measuring device communications function 416, a controller 418, and a memory 419. RFID module 410 can be configured to store identification information for device 402 and module 404. Further, RFID module 410 can store identification information for electronically keying device 402 with module 404. RFID module 410 can also identify the subject 150 and the sensors or measuring devices 402 and responding/reaction devices like massaging, vibration, light dimming devices including headphones 20 to aid in assembling and matching the right parts to the right subjects 150. In this case each system is tuned for a particular individual and the responding/reactionary devices can be integrated with the measuring devices 402.

Communications module 404 can further receive a polling signal for identification and/or parts/inventory information from networks other than a typical RFID short range response. In response to receiving a polling signal, the identification, inventory, and/or routing information can be retrieved from RFID module 410 and sent to an originator of the polling signal anywhere on the globe. Transceiver 412 can include an antenna 420 for communicating wirelessly. A polling signal can be received from a network-enabled device. The response to a polling request may be disabled if the originating signal does not contain the appropriate authenticated identification in order to prevent eavesdropping or tampering with the confidential information that transmits between parties. Various data and programs can be stored in memory 419.

In one embodiment, the communication channel may enable a virtual private network that enables confidential transmission of key information between parties. Communication module 404 may contain all the necessary confidentiality/key protocols and encryption and authentication techniques that are well understood by those knowledgeable in the art. Examples of authenticating a request include passwords, pass cards, digital signatures, and biometrics, such as fingerprint, retinal scans, face scans, and voice identification and such. In multifactor authorization, there may be multiple tests to secure the transfer of information. For instance, you may have a token, a password, and a biometric identification, such as a fingerprint.

In another embodiment, communications module 404 can be configured in a direct notification system such that a central computer system (such as central computer system 497) can monitor a position/location of measuring device 402 by receiving position/information location from locating device 414.

Controller 418 can include suitable hardware, software, and/or firmware components for managing the components of module 404. Further, controller 418 can include suitable memory for storing software and identification, inventory, and/or routing information. RFID module 410 can be distributed for use in association with a particular measuring device by a third party.

Locating device 414 can determine a position/location of measuring device 402 and/or communications module 404. A position/location can be determined by any suitable technique such as GPS. In one embodiment, locating device 414 can be configured to determine a position/location of measuring device 402. Communications module 404 can communicate the position/location of measuring device 402 to network-enabled devices in communication with communications network 406.

Communications module 404 can include a tracking system 422 configured to store tracking information associated with measuring device 402. In one embodiment, the tracking information can include identification information for measuring device 402. For example, tracking system 422 can retrieve identification information for measuring device 402 that is stored and shared with RFID module 410.

Further, communications module 404 can determine whether the position of measuring device 402 is within the predetermined boundary. For example, communications module 404 can determine whether the distance between the position of measuring device 402 and the predetermined boundary is equal to and/or greater than a predetermined distance. In this example, if it is determined that the distance between the position of measuring device 402 and the predetermined boundary is equal to and/or greater than a predetermined distance, communications module 404 can transmit a notification signal or alarm to a network-enabled device connected to network 496, a base station, and/or central computer system.

In another embodiment, communications module 404 can determine diagnostic information and training or service information of measuring/responding device 402. The diagnostic and training information along with the health of the sensors, responding devices and systems can be communicated to a remote device according to the techniques described herein. This could result in the alarm state related to the health of the instrument being triggered.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium (including, but not limited to, non-transitory computer readable storage media). A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++, Python or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter situation scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function (s). It should also be noted, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for predicting and responding to a subject's physiological state using a machine learning (ML) model, comprising:
    collecting at least one of physiological data and biometric data from the subject via a plurality of sensors;
    operating in a learning mode, wherein operating in the learning mode includes:
        training the ML model using a training dataset comprising a first subset of the at least one of the physiological data and the biometric data, wherein the training includes:
            labeling physiological data points where the subject exhibits particular physiological states and associating these data points with corresponding stimuli; and
            optimizing ML model parameters by minimizing a loss function between predicted outputs and actual outputs using at least one of: gradient descent, backpropagation, or adaptive optimization algorithms;

operating in an operational mode, wherein operating in the operational mode includes:

inputting a second subset of the physiological data into the trained ML model, wherein the trained ML model processes the second subset of the physiological data to detect patterns of behavior and classify the subject's physiological state;

predicting that a current physiological state of the subject will transition to a future physiological state using the trained ML model based on the classification and a relationship between patterns of behavior at different times;

generating an output signal corresponding to a stimulus that modifies the subject's physiological state to avoid the predicted transition to the future physiological state, wherein the stimulus is selected from stimuli including auditory signals, vibrations, visual stimuli, haptic feedback, or electrical stimulation; and delivering the selected stimulus to the subject via at least one stimulus device configured to deliver the stimulus based on the output signal; and operating in a closed-loop feedback control mode during the operational mode, wherein the closed-loop feedback control mode comprises:

measuring a physiological response of the subject after delivering the selected stimulus;

determining whether the measured physiological response indicates improvement in the subject's physiological state toward a baseline range for the subject;

in response to determining that the measured physiological response indicates improvement, maintaining stimulus parameters while the subject's physiological state continues to improve;

in response to determining that the measured physiological response does not indicate improvement, updating the ML model parameters based on the measured physiological response and the delivered stimulus, generating an output signal corresponding to a different stimulus based on the updated ML model, and delivering the different stimulus to the subject; and iterating the closed-loop feedback control mode during the operational mode such that stimulus selection is refined based on the measured physiological responses of the subject.

2. The method of claim 1, wherein the optimization of model parameters includes using an adaptive optimization algorithm selected from Adam, Adadelta, Adagrad, Root Mean Squared Propagation (RMSProp), or Stochastic Gradient Descent (SGD) algorithms.

3. The method of claim 1, wherein collecting the at least one of physiological data and biometric data includes using at least one of a: EKG sensor, ECG sensor, EEG sensor, infrared temperature sensor, acoustic sensor, accelerometer, brain wave sensor, vibration sensor, sound sensor, movement sensor, breathing sensor, eye movement sensor, cardiovascular monitor, core temperature measurement sensor, ear measurement sensor, and pulse sensor for measuring at least one of heart rate, temperature, heart rhythm, respiratory rate, audio measurements, muscle activity, oxygen levels, and motion data.

4. The method of claim 1, wherein the loss function minimized during training is a cross-entropy loss function.

5. The method of claim 1, wherein the ML model utilizes embeddings to represent categorical data including at least one of: specific types of stimuli or subject identifiers.

6. The method of claim 1, wherein the updating of the ML model includes adjusting the weights of some layers of the ML model while keeping other layers fixed.

7. The method of claim 1, wherein delivering the selected stimulus to the subject includes mediating a sensory input of the subject.

8. The method of claim 7, wherein mediating the sensory input of the subject includes playing at least one of music, sound, or voice for the subject.

9. The method of claim 7, wherein mediating the sensory input of the subject includes at least one of suppressing and alternating external environmental sounds.

10. The method of claim 1, further comprising preprocessing the collected physiological data using at least one of: data cleaning, feature extraction, point-wise nonlinearities, or embeddings.

11. The method of claim 10, wherein the preprocessing of the physiological data includes applying point-wise nonlinear transformations.

12. The method of claim 1, wherein the ML model comprises a deep learning architecture with multiple hidden layers, including at least one of a Long Short-Term Memory (LSTM) network, a Recurrent Neural Network (RNN), or a Transformer model to capture temporal dependencies in the physiological data.

13. The method of claim 1, wherein the stimuli are selected based on probabilities associated with different stimulus intensities, and the ML model outputs a probability distribution over possible stimuli.

14. The method of claim 1, wherein the stimulus device comprises a smart wearable configured to deliver haptic feedback with adjustable amplitude and frequency.

15. The method of claim 1, wherein the ML model is trained using transfer learning techniques that utilize pretrained models from other subjects.

16. A system for predicting and responding to a subject's physiological state using a machine learning (ML) model, comprising:

a plurality of sensors configured to collect at least one of physiological data and biometric data from the subject, the physiological data including at least one of heart rate, respiratory rate, temperature, heart rhythm, respiratory rhythm, audio measurements, muscle activity, oxygen levels, EEG, EKG, and motion data;

at least one processor coupled to a memory storing executable instructions, wherein the processor is configured to:

operate in a learning mode that includes configuring the processor to:

train the ML model using a training dataset comprising a first subset of the at least one of the physiological data and the biometric data, wherein the training includes:

labeling physiological data points where the subject exhibits particular physiological states and associating these data points with corresponding stimuli;

optimizing ML model parameters by minimizing a loss function between predicted outputs and actual outputs using at least one of: gradient descent, backpropagation, or adaptive optimization algorithms;

operate in an operational mode that includes configuring the processor to:

input a second subset of the physiological data into the trained model, wherein the trained ML model processes the second subset of the physiological data to detect patterns of behavior and classify the subject's physiological state;

predict that a current physiological state of the subject will transition to a future physiological state using the trained ML model based on the classification and a relationship between patterns of behavior at different times;

generate an output signal corresponding to a stimulus that modifies the subject's physiological state to avoid the predicted transition to the future physiological state, wherein the stimulus is selected from stimuli including auditory signals, vibrations, visual stimuli, haptic feedback, or electrical stimulation;

operate in a closed-loop feedback control mode during the operational mode that includes configuring the processor to:

receive updated physiological data from the plurality of sensors after delivering a stimulus to measure a physiological response of the subject;

determine whether the measured physiological response indicates improvement in the subject's physiological state toward a baseline range for the subject;

in response to determining that the measured physiological response indicates improvement, maintain stimulus parameters while the subject's physiological state continues to improve;

in response to determining that the measured physiological response does not indicate improvement, update the ML model parameters based on the measured physiological response and the delivered stimulus, generate an output signal corresponding to a different stimulus based on the updated ML model for delivering the different stimulus to the subject; and iterate the closed-loop feedback control mode during the operational mode such that stimulus selection is refined based on the measured physiological responses of the subject; and at least one stimulus device configured to receive the output signal and deliver the stimulus based on the output signal.

17. The system of claim 16, wherein the plurality of sensors includes at least one of a: EKG sensor, ECG sensor, infrared temperature sensor, accelerometer, brain wave sensor, vibration sensor, sound sensor, movement sensor, breathing sensor, eye movement sensor, cardiovascular monitor, core temperature measurement sensor, ear measurement sensor, and pulse sensor.

18. The system of claim 16, wherein the system is configured to mediate a sensory input of the subject.

19. The system of claim 18, wherein mediating the sensory input of the subject includes playing at least one of music, sound, or voice for the subject.

20. The system of claim 18, wherein mediating the sensory input of the subject includes suppressing external environmental sounds.

21. The system of claim 16, wherein the ML model comprises a deep learning architecture with multiple hidden layers, including at least one of a Long Short-Term Memory (LSTM) network, a Recurrent Neural Network (RNN), or a Transformer model to capture temporal dependencies in the physiological data.

22. The system of claim 16, wherein the stimuli are selected based on probabilities associated with different stimulus intensities, and the ML model outputs a probability distribution over possible stimuli.

23. The system of claim 16, wherein the stimulus device comprises a smart wearable configured to deliver haptic feedback with adjustable amplitude and frequency.

24. The system of claim 16, wherein the ML model is trained using transfer learning techniques that utilize pre-trained models from other subjects.

25. The system of claim 16, wherein the optimization of model parameters includes using an adaptive optimization algorithm selected from Adam, Adadelta, Adagrad, Root Mean Squared Propagation (RMSProp), or Stochastic Gradient Descent (SGD).

26. The system of claim 16, wherein the updating of the ML model includes adjusting the weights of some layers of the ML model while keeping other layers fixed.

27. The system of claim 16, wherein the ML model utilizes embeddings to represent categorical data including at least one of: specific types of stimuli or subject identifiers.

28. The system of claim 16, wherein the loss function minimized during training is a cross-entropy loss function.

29. The system of claim 16, wherein the processor is configured to preprocess the collected physiological data using at least one of: data cleaning, feature extraction, point-wise nonlinearities, or embeddings.

30. The system of claim 29, wherein the preprocessing of the physiological data includes applying point-wise nonlinear transformations.

* * * * *